(12) United States Patent
Fremaux et al.

(10) Patent No.: US 8,236,550 B2
(45) Date of Patent: Aug. 7, 2012

(54) **GENETIC CLUSTER OF STRAINS OF *STREPTOCOCCUS THERMOPHILUS* HAVING APPROPRIATE ACIDIFYING AND TEXTURIZING PROPERTIES FOR DAIRY FERMENTATIONS**

(75) Inventors: Christophe Fremaux, Poitiers (FR); Pascal Fourcassie, Poitiers (FR); Elise Manoury, Chatellerault (FR); Philippe Horvath, Scorbe-Clairvaux (FR)

(73) Assignee: Danisco A/S, Copenhagen (DK)

( * ) Notice: Subject to any disclaimer, the term of this patent is extended or adjusted under 35 U.S.C. 154(b) by 560 days.

(21) Appl. No.: 12/443,903

(22) PCT Filed: Oct. 2, 2007

(86) PCT No.: PCT/EP2007/060463
§ 371 (c)(1),
(2), (4) Date: Apr. 1, 2009

(87) PCT Pub. No.: WO2008/040734
PCT Pub. Date: Apr. 10, 2008

(65) Prior Publication Data
US 2010/0184181 A1 Jul. 22, 2010

(30) Foreign Application Priority Data

Oct. 3, 2006 (FR) .................................. 06 08657

(51) Int. Cl.
*C12N 1/20* (2006.01)
*A23C 21/00* (2006.01)
(52) U.S. Cl. .................. 435/253.4; 435/252.1; 426/583
(58) Field of Classification Search .................... None
See application file for complete search history.

(56) References Cited

OTHER PUBLICATIONS

Senini et al. EPS phenotype and genotype in *Streptococcus thermophilus* strains of dairy origin. Annals of Micro. 54(1): 59-71, 2004.*
International Search Report in PCT/EP07/60463 dated Jan. 21, 2008.
Broadbent et al., J. Dairy Sci., 86:407-423 (2003).
Jolly et al., Int. Dairy J., 11:733-745 (2001).

* cited by examiner

*Primary Examiner* — Michele K Joike
(74) *Attorney, Agent, or Firm* — McAndrews, Held & Malloy Ltd.

(57) ABSTRACT

The invention relates to a genetic cluster of strains of *Streptococcus thermophilus*, which have a lysotype distinct from that of the strains currently used. Within this cluster novel acidifying and texturizing strains have been identified.

13 Claims, 4 Drawing Sheets

Fig. 2A

Figure 1:
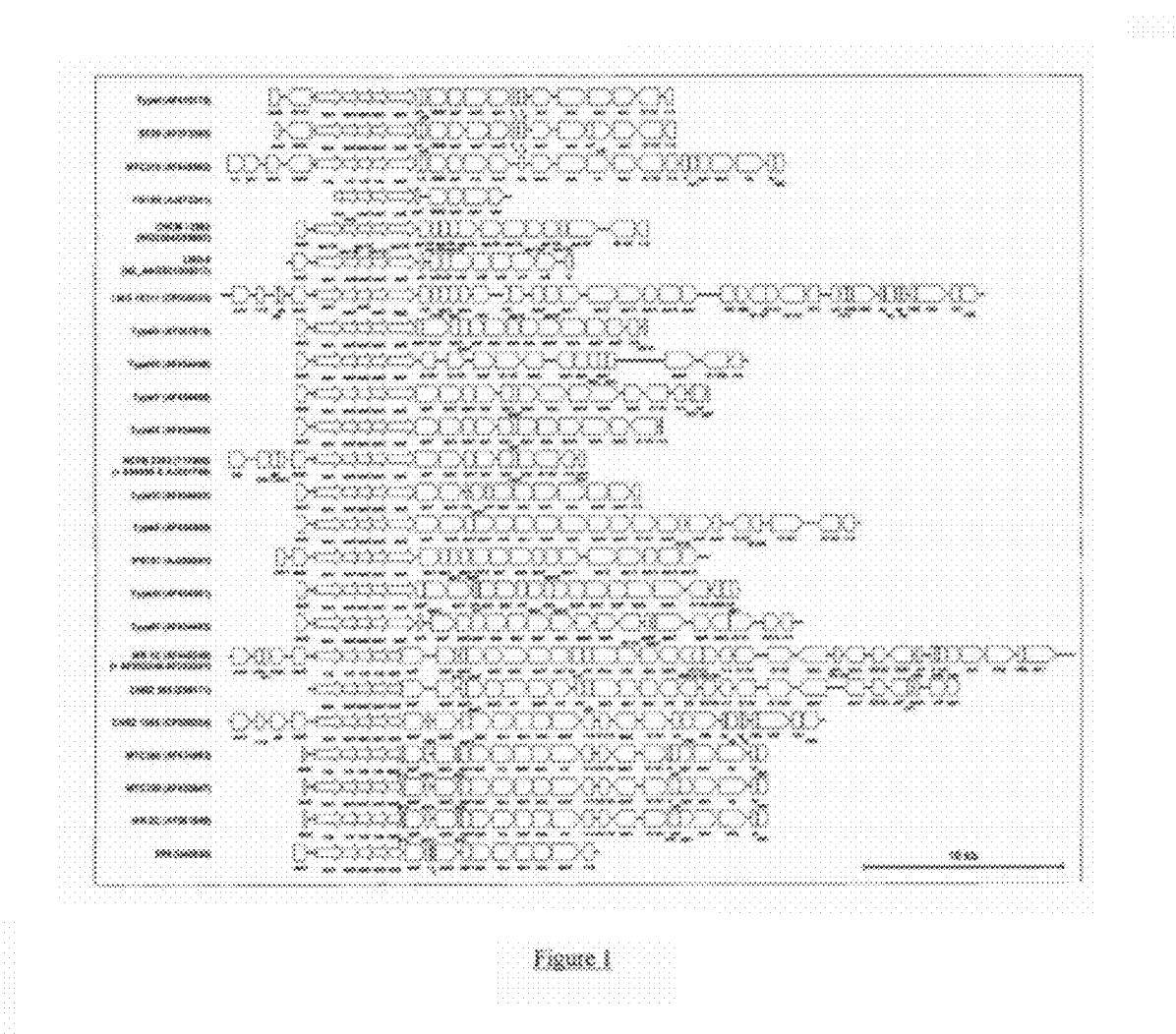

SEQUENCE LISTING

```
<160> NUMBER OF SEQ ID NOS: 61

<210> SEQ ID NO 1
<211> LENGTH: 24
<212> TYPE: DNA
<213> ORGANISM: Streptococcus thermophilus

<400> SEQUENCE: 1
aaatgaattc agagcaagca cttg                                          24

<210> SEQ ID NO 2
<211> LENGTH: 24
<212> TYPE: DNA
<213> ORGANISM: Streptococcus thermophilus

<400> SEQUENCE: 2
gtcatgtcaa ctttattaag gacg                                          24

<210> SEQ ID NO 3
<211> LENGTH: 16037
<212> TYPE: DNA
<213> ORGANISM: Streptococcus thermophilus

<400> SEQUENCE: 3
agttgattga ccaacttggt ggtgtgacag tccataatga tcaagctttc acaagtcttc    60
atgggaagtt tgatttccca gttggagata tccaaatgaa ttcagagcaa gcacttggat   120
ttgttcgtga acgctatagt ttagatgacg gagataatga ccgtggtaaa aaccaggaga   180
aagtcatttc tgcgattgta aacaagttgg cttctctaaa gtctgtatca aactttactt   240
```

-continued

```
caatcgttaa taatctccaa gactctgttc agacaaatat ttctttggat accattaatg      300
ctttggctaa tacacaactt gattcaggct ctaaatttac agtaacgtct caagcagtaa      360
ctggtacagg ttcaaccgga caattgacct cttatgctat gccaaattct agtctttaca      420
tgatgaaact agataattcg agtgtggcaa gagcctctca agctatcaaa atctgatgg       480 aggaaaaata agtgattgac gttcactcac atattgtttt tgatgttgat gatggtccta     540
aaactttaga agaaagttta gacctcattg gtgaaagtta cgcccagggg gtacgtaaga     600
ttgtttcaac atcccatcgt cgtaagggaa tgtttgagac tccagaggat aaaattttg      660 ccaactttc taaggtaaaa gcagaagcag aagcactta tccagactta actatttatt       720
atggaggtga actttattac accttagaca ttgtggagaa acttgaaaag aatctcattc     780
cgcgcatgca caacactcaa tttgctttga ttgagtttag tgctcgcaca tcttggaaag     840
aaattcatag tgggcttagt aatgttttga gagcgggggt aacgcctatt gttgctcata     900
ttgagcgcta tgatgccctc gaagaaaatg ctgatcgtgt tagagaaatc atcaatatgg     960
gctgctatac tcaagtcaat agctcacatg tcctcaaacc aaagctcttt ggagataaag    1020
ataaagtagg aaaaaaacgt gttcgttatt tcttggagaa aaatttggtt catatggttg    1080
ctagtgacat gcataatctt ggtccaagac caccatttat gaagatgct tatgaaattg     1140 ttaaaagaa ctacggctcc aaacgtgcta agaatctttt tattgaaaat cccaaaacat     1200
tactagaaaa tcaatattta taggagatat tatgaatcaa gataacacta aaagtgatga    1260
aatcgacgta ctagcattgc tacataaact tggacgaag aagcttttga ttcttttcac      1320
agttttttat ttcgctgctt tcagtttctt aggtacttat ttctttatcc aaccaacata    1380
tacatcaaca acgcgtatct atgtggttaa tcaggcaaca gataataaga atctttctgc    1440
tgaagctttg caggccggta cattttttgac aaaagactac aaagaaatta ttacatcaaa    1500
cgatgtcttg tcagaagtta tcaaagatga aaaattgaat atgacagtag cagaacttgc    1560
taaaatgatt ttagttgata atcctactga tactcgtctt atttcaattt ctgttaatgc    1620
taaaactggt caagatgcgc aaacacttgc caataaggtt cgtgaagttg cttcagaaaa    1680
aatcaagaac gtgacaaaag ttgaagatgt tacaacgctc gaagaagcta aattgccaga    1740
gtcaccatct tcaccaaata tcaaacttaa tgtgcttctt ggggcagtgc ttggaggatt    1800
ccttgcagtg gttggtgtat tggtacgtga aatcctagat gatcgtgttc gccgtccaga    1860
agatgtggaa gatgcccttg gaatgacact tcttggaatt gtccctgata cagataaaat    1920
ttaaggagaa gaaatgcctc tattaaagtt agtaaaatct aaagtaaact tgccaaaaca    1980
aacagaagag aattacaatg ccattcgcac aaatattcaa ttttctggtg ctcagattaa    2040
agtgattgcg attagctctg ttgaagctgg tgaaggaaaa tcaacgacat ctgttaactt    2100
ggcgatttca tttgctagtg ttgggctccg aacacttctg attgatgctg atacgcgtaa    2160
ttctgttttg tcgggtacat ttaaatcaaa tgagccttat aaaggtcttt caaatttcct    2220
ttcaggaaat gccgatctaa atgaaacgat ttgccaaact gatatttctg gtttggatgt    2280
tattgcatct ggtcctgttc cacctaatcc aacaagtctt ttgcaaaatg acaattttag    2340
acatttgatg gaagttgctc gtagtcgtta tgattatgtc atcatcaata caccaccaat    2400
tggtatggtt attgatgcag ttattattgc ccatcaggct gatgccagtc ttttggttac    2460
agaaggtggg aaaatcaaac gtcgtttcgt aactaaggcc gttgaacaat ggaacaaag     2520 tggttctcag ttccttagggg tcgtccttaa taaagttgac atgacagttg ataaatatgg    2580
atcatatggt tcttacggat catatggcga gtatggaaaa aaatctaacc aaaaagaagg    2640
```

```
tcattcaaga gcacatcgtc gtagaaaagg atagcattaa tggggatgat gcggttcctt    2700
ataccttaac agattaaaaa ggggtttaga gtgaaagaaa aacaagaaat tcatcgcatt    2760
gaaattggta ttatacagtt ggttgtggtt gttttcgcag ccatggtagc tagtaaaata    2820
ccttatacag agattaccca aggaagcatt gtccttttag gtgtcgtaca tgtagtgtct    2880
ttctatatca gtagttatta tgaaaatctt aagtatagag gctacttgga tgaactcatt    2940
gcaactgtca atattgtttt catatttgct ctaattgcaa cttttcctctc gttttttgca    3000 gatggaagtt tttctatctc acgtcgcgga cttcttatg ttactctgat tcaggtgtt      3060 ctcttatacg ttacaaatac tgttcttaag tatttccgct cttctattta tacacgtcgt    3120
aaaagcaata agaatattct cttgatttct gatcaggcac gtcttgataa tgttttgtct    3180
cgtatgaaag acaatatgga tggtaggatt acagccgttt gtgtcttgga taatccttat    3240
ttcacggatc catttatcac gagtgttaaa cctgaaaatt tgattgaata tgcgacacac    3300
tcagtagtag accaagtttt gattaatctg ccaagtgggc agtataagat ttgggattat    3360
gcatcacctt ttgagatcat gggaattcca gtttctatta atttgaatgc ccttgaattt    3420
atgagtcaag gtgaaaaacg tattcaacaa ttggggcctt tcaaagttgt tacgttttca    3480
actcaatttt atagctatgg agatgtcttg gcgaaacgtt tcctcgatat ctgtggagcc    3540
ctagttggtt tggtgctctg tgggattgtt ggaatcttcc tttatccact tattcgtaag    3600
gatggtgggc cagccatttt tgctcaagac cgtgtgggag aaaatggacg tatcttcaag    3660
ttttataaat tccgttctat gtgtgttgat gcggaagaaa tcaagaagga tttgatgaca    3720
cagaatcaaa tgtctggtgg tatgtttaag atggacaatg atccacgtat taccaaaatt    3780
ggacatttca ttcgtaaaac gagtcttgat gaacttccac aattttggaa tgttctaaaa    3840
ggtgatatga gcttggtagg aacacgtcca ccaacattgg atgagtacga atcttataca    3900
ccggaacaaa aacgtcgcct cagctttaaa ccaggtatta ctggtctttg gcaagtaagc    3960
ggtcgaagtg aaattactaa ttttgatgaa gttgtaaaac tagacgttgc ttatttggac    4020
ggatggacaa tctggcgaga tatcaaaatc ttattgaaaa cgattaaagt agtagtaatg    4080
aaggatggag caaagtaatg gctttctcca tttcttttaa tgttgattaa atgacaaaaa    4140
cagtttatat cgttggttct aagggggattc agcaaagta tggtggtttt gagacttttg    4200
tagaaaaact aacggcacat caaagtaata aaaaccttaa gtatcatgtt gcttgtttat    4260
cgaatggtat acaagaaaat tttaatcata atgatgcaga ctgttttaat atttcaaaga    4320
aaaatattgg accagcaaac gccatttatt atgatttggc agctttaaaa tactcactta    4380
aagaaattgt agaaaatagg tatgagggtg caattattta cattttagct tgtcgtattg    4440
gtccatttat tggtcactat aaaaagcaaa tgaaaaaatt aggaattact ttgatggtaa    4500
atcctgatag ggagtgtgaa ataatatggg caaccagaca aaagcctgat ttcatgcggg    4560
tttacgcggc ttgacctttt cacctcaacc tatttctgcc tgtcatggtg tgttgcggcc    4620
ggtttcatag gttctaacct tgtgaaacga atttatcagg aggctccttc tgctacggtt    4680
atcggcatcg acaacatgaa tgcctactat gatgtggcac tgaaagagtt cagcctgaat    4740
gagctggcca agtatcccac atttaccttt atcaaaggca acatcgccga caaggagctg    4800 atcacgagc tgttcgagaa gtacaagccg tctgtggtcg tcaaccttgc tgcacaggct    4860
ggtgtgcgtt acttcatcac caaccccgga tgctatgtgg aatctaacct ggtcggcttt    4920
ttcaatatcc ttgaagcatg ccgcattgc gagaagagtc tagagcatct ggtttacgcc    4980
tcctcctcca gcgtttacgg ttccaataaa aaggttccgt atagcactaa cgacaaagtg    5040
```

```
gacaatcctg tctctctgta cgcagcaacc tagaagtcta atgagctgat ggctcacgct    5100
tactccaagt tgtacaacat tccgtctact ggtctgcgct ttttcacagt gtatggtcct    5160
gcaggtcgtc cggacatggc ctacttcgga ttcaccaaca agctggtgaa gggcgaaacc    5220
atcaagattt tcaactatgg aaactgcaag cgtgatttta cttatgtgga tgacatcgtt    5280
gagagtgttg tccgtgtgat gaagaaagca ccggacaaga aaaatggtga agatggtttg    5340
ccgattccgc cgtatgcagt ttacaacatt ggtaatctga accctgagaa cctgctagat    5400
ttcgtgcaga ttctgagtga ggagttagta agagcgaaag ttctgccgga agattatgac    5460
ttcgaggcac acaaggaact tgttccgatg cagccgggtg atgtgcctgt gacctatgca    5520
gataccagcg cactggagcg tgacttcgga taaaagccga gcacaagtct gcggactgga    5580
ttaagaaatt ttgctgagtg gtacgctgag ttttataaat aaaagaatta gaggaataga    5640
gaaatgagaa agtttaaaga tttaaagatt gctgtggctg gtactggtta tgttggtctt    5700
tctattgcta cgttgctgtc tcagcatcac aaggtgacgg cagtagatat cattcctgag    5760
aaagtagagc tgatcaataa caagaagtct ccgattcagg atgagaacat tgaaaagtat    5820
ctggcagaaa aggaactgga tctgaccgca acgttggatg cgaaggaagc atacagtgat    5880
tctgattttg tcgtaatcgc tgcaccgaca atgtctactc aacaaaccat attgacgtag    5940
aaacgtcgaa aagaacctgt tttgcacact atataggca ctgaaattgg ttatatttca    6000
cagctatatg agctataaat gctagatact tatacaaaat gctgaacttt tggcccatgt    6060
ggcacaaaat tggcacatct ttttcagaag aatcatagaa atggcggaaa acaggagaaa    6120
acaacaaaaa tccatgaatt tatcattaac gtctgaaact gctgttgagt acactatctg    6180
acccgctaat gacacctaca tcataacggt ttgttgagtc atgaaaaata gagaaaaaca    6240
gatgatttct acttcaaaaa acagctgttg agtagagcat gaatggtgat gataattaca    6300
tgttttgagt ggttaaagtg aatgatttgt tcataacgaa caatgaatgg tgagaattgg    6360
actggatgat atatacagtt ttaacaaaac tcatgtgccg acagggttcg attcaacaat    6420
ccaacactta gaaaaacgtc attgcagggt atacgggggt cgactgtata atcaacact    6480 tcggttatag aggaatagag acgagtgtac tcaacggatg ttttatgaag tagaaacatg    6540
attgcggggg taattggata cgacagtata agaaaacact tagccgtgtg atgaacacac    6600
gggagaatta gagagaaata ccatccaatg aggatgtgta gatagatata aaaatgagga    6660
atgaacccag taagagtgga ggagtacatt atggaaaaat ttgattattt agtagtaggt    6720
tctggccttt acggggcgat ttttgcacat gaagccaaga atcatggaaa atctgtttta    6780
gtagtagata agtgtcctaa cattgcggga aatatctata ccaaaaacat tgagggtatc    6840
aatgtccata aatatggagc gcatattttc cacactaaca acaaaaaggt ctggaactac    6900
attacacagt ttgctgagtt caaccgcttc accaactccc ccgtgccaa ctacaaaggc    6960 gagctgtatt cgctgccttt caacatgtat acatttaata aaatgtgggg cgtcgtgacg    7020
ccggaggaag ctgccaccaa aatcgcggag caacgcaagg aaattactca tgagcctcag    7080
aatctcgaag agcaggccat ttctcttgtc ggccgtgata tctacgagaa acttattaag    7140
ggctacactg agaagcagtg ggggcgcgat tgtaaagagt tgccgtcctt tattattaag    7200
cgtcttccgg ttcgcctgac ttttgataac aactacttca atgcgcttta tcagggtatc    7260
cctgtcggtg gttataccaa gatgattgct aatctgctgg atggcattga ggttcgtttg    7320
aatacagact atctggcgaa caaggtagag ttggatgcat tggctgacaa ggttgtatac    7380
actggaccga ttgatgctta cttttgactat cagttgggta cattggaata ccgatctgtt    7440
```

```
cgctttgaaa cggaaacatt ggacaagcct aattttcagg gtaacgcagc agtgaattat   7500
accgaccgtg aaactccgtg gactcgcatc attgagcata aatggtttga gtttggcaag   7560
gatgaaaatg gcaatgatct gccaaagact atcatcagcc gtgagtacag cagtgagtgg   7620
aagccgggag atgagccgta ttatccggtc aacgatgcta agaatagctt gctttattct   7680
gagtataaga agctggcaga tgcagaagaa aaagtaatct tcggcggtcg tcttggcgag   7740
tataagtatt atgatatgga ccaggtaatt gcagctgtgt tggataaatg caagaaggag   7800
ctgggagaat aaaatggcaa agaaaaagat tttaatggtc tgtgaagctt ttggaggtgg   7860
agtatttacc tatgtatctc aactctgcaa cgatatggtg gatgattttg acgtttatct   7920
tgcatattcc ctcagaccgc agacccctaa gaattacaaa gattttctgg atcagagagt   7980
gcatttgatt gaaatgcaaa atgtcggagt taagggacta acaaacttaa agagtgacat   8040
tgcagcaatt aaggaattgc gtcagattga aaaagatgtt cagccagatg tgattcacct   8100
gcattcttcg gttgcaggtg gtttaggtag acttgcatat aacggaaaaa ataatactgt   8160
tgtgtacaca cctcatgggt atgcacatat tcttatgggt ccggggaaga agagaaaagt   8220
ctataagttt gcagaaaagg ttctcggaaa tcgagcactt acacttacct gttgcgaaag   8280
tgaagatgaa gaagcaaaga aattctccaa gagaacagct tatgttgaaa cgggtgtgaa   8340
tcttgcagac ctttcggcat cccttgacgg tattaagcct gtaaaaaatg ataagttcac   8400
agttttacg cttggtcgcg cctgcgttca gaaacagcca cagcttttta atagaattgc   8460
tgaactagta ccagatgcaa gatttatttg gattggtaac ggagaacttg aaaatgagtt   8520
aactgctcca aatattgaag tgacgggatg gaaacctcgt aaggaagctt ggcaatggc   8580
caaaggtgca gatgcatta ttttgtgcag tcttggtgaa gctattgcaa tgagccttat   8640
tgagaatatg tacattaaaa agctgattct cgttagcaat acaatgggaa ataagagtgt   8700
tatcaatgat ggcatcaatg gatatgtctg tgataaggcg gaggagtatg ctgaacatat   8760
aaaagcggct atgaaggagt ttcctaaaga acttcctgaa agagcatatc aggatgtcct   8820
tgagatttat aatactgatg ccatgaagaa gaagtatatt gagttttata atgatgttgt   8880
ggcaggtaaa tactgatgat aaaaaatatg gactatttag tttccgtcat tgttcccata   8940
tacaaagtgg aaaagatttt gtcggattgc gttctgagca tttgcaatca gacctataca   9000
aatttagaga ttattcttgt tgatgatggc tctccagata attgtggaca aatgtgtgat   9060
gaatttgcaa aaaatgatgt ccgaataaag gttattcata aaattaatgg agggttatca   9120
caagctcgaa atgctggaat gagcattatg acgggagatt atattacatt tgttgatagc   9180
gatgacattt tggaacatga atttattgaa gaaatgttga ggataattaa taaatataat   9240
gctcaagttg caatttgcaa aaattctaca tttgaaaaag gcggtacact taataatggt   9300
catgtaggaa taagcgaacg aagctttgat gcggtagaag ccataaagaa catgttatat   9360
caaaaggatt ttgatgttgc agcatgggga aaaatgtaca tcaaaaaata cgaaaatgcg   9420
ctgaatgaac gggggtata gcatgactta attcgtttta ttgcggttgt caggccgtac   9480
acccttgcat actctgttag tattgagcca gataattatg gcactgcaaa ggcggtggca   9540
tgatgaaaaa gataaggatt ttacatgtag cgcaagctgc tggcggcgtg gatcgctaca   9600
tccgaatgct tctcaagcat ttggataagg aaaaatttga gaatatactg gtttgctcac   9660
aggatttcct tgaggaagat tatagaggat tggttgattc ttttgaacga atcgaaatga   9720
ccagagctat tggtggcaac gacttaaaag caattaaaga agttagaaat ctgataaaga   9780
aatataaccc tgacattgtt tatgctcact ccagtaaggc tggagccatt gcccgtgttg   9840
```

```
ccgatatcgg tttgaaaaat tactgtgtat ataacccaca cgggtgggca tttaacatgc    9900
gttgttctgc aaagaaaaaa gcaatataca cggctattga aaagattgct gctccattct    9960
gtgaaaagat tatctgcatt tcggatgcgg agaggcagtc agcattggat aaaaaaatat   10020
gcaaagaaga taagttacag gtcattttta acggtgtgga tatcgaggcc tacgaaaatg   10080
gagtacatgg cgctgttaag agagaagacc tgaacatacc ggatgatgca tttgttgtcg   10140
gcatggttgg acgaatgagc ccacagaaag caccagatgt ttttgttaag atggcaaagc   10200
aagtaaagga gaaagttttg aatgcacact tcattattgt tggcaacgga aatcaagaag   10260
ccgaaattag aaagtatgtg gaggacaatg gtttctcgaa cagcctgcat attacaggct   10320
gggttgataa aacgttgcag atgtctgcaa gaagatggat tgcaaaatga cctacatcag   10380
cacagactat gtgttcgatg gtcagggtac cgagccttgg cagccggact gcaaggatta   10440
caagcctttg aatgtgtacg gtcagacgaa gctggaaggt gagttggcgg ttagccagac   10500
gttggagagg tatttcattg tccgcattgc atgggtattt ggtctgaatg gtaagaactt   10560
catcaagacg atgctgaatg tcggcaagac acacaatact gtccgtgtgg tcaatgatca   10620
gatcggtaca ccgacctata catacgattt ggctcgactg ctcgtcgata tgaatgagac   10680
tgagaagtat ggctattacc atgcgaccaa cgagggtggt tatatcagct ggtacgattt   10740
aacgaaagaa atttatcgtc aggtgggcta taagacagca gaggtgcgtc cggtaagtac   10800
ggaagagtat gtcctgagta aagcaactcg cccgtttaac agtcgtctgg ataagagcaa   10860
gttggtagaa gctggcttta ctctgcttcc gacctggcaa gatgcgctga gccgttacct   10920
gaaagaagtt gagcagtaag aggagataga aagatggga cagataaaag ttgagaaaaa   10980
tgtaggcggt atcgaaggac tttgcgttat tgaacctgct gttcatggcg atgctcgtgg   11040
ctatttcatg gaaacctaca acgaaaaaga tatgaaagaa gcaggcattg acatccactt   11100
cgtgcaggac aatcagtcta tgtccactaa gggcgttctg cgcggtttgc atttccagaa   11160
gcagtatccg cagtgcaagc tggtacgcgc catgcgtggt actgtgtttg atgttgcggt   11220
tgacctgaga agtgattcta agagttacgg caagtggtat ggtgttacac tgtccgctga   11280
gaacaagaag cagttcctca ttccagaggg atttgcgcac ggtttcctgg ttctgagcga   11340
tgaggcagag ttctgctata aggtcaacga cttctggcat ccgaatgacg agggtggcat   11400
ggcttggaac gacccggaga taggcattga gtggccggaa ctgaagggcg agtataaggg   11460
cagcgcaagt gctgaaggct acacgctgaa agatggtact gcattgaact tgagcgataa   11520
ggaccaaaag tggctgggac tgaaagatac ttttaaattt taaggataag gaataatcga   11580
tgaagatatg ttcaatagtg gttctatatg agcctaataa caaagaaata gaaaatattc   11640
tggattatta tgacagcgtt gataaagcat atattttaga caactcagtt gaaagcagag   11700
aagcaattgt aaatgatgtt ttatcgaagc gtagtgggta tgtcaaagaa aaagcggagt   11760
acatccattt ccataaaaac attggtttat gcaaagcatt aaaccatgga atgaaactgg   11820
cggcagatga aggctttgaa tgggctctta ttatggatgc cgatagtacc ttcaatacta   11880
atgttgtgaa agtatataaa gattatatcc aaaagaataa ctgcagtaaa ataggtgtcc   11940
ttgcgccagt acatcttcat gatagaaacc ttgagagtaa atttgaagga caaagagatg   12000
tgtcttgggc gatgacatct ggatgctttt ataatatcag cgtgtttgaa actgctaatg   12060
ggtttaaaga ggaacttttt gtagacggtt tggatataga ttattgctat aaaatgcata   12120
gatatgggta tcgcgtagta gaacttgcgg atgcccgaat taatcatttg ccagctgaaa   12180
ctcgcatgtt taatcttggt ggatttaaag taaaatatgg tgtggcttca ccgtggcggt   12240
```

```
attacatgca agctagagca atagtttggt tggcactgga gtataagtcg ctaagggagg    12300
tagctcgata ctgcgtgaaa tggggaaagg tacttctctt gtttgataat aagacggatt    12360
acataaaaca acttatgcat ggaactaaag atgggataaa actatggaga agtattcact    12420
gagtggaata gttttatgac gttttattat gatttagaca tagttattat cagaaataga    12480
taaaataccg tatcaattca atggaggata tattacacat ggacatatca gcgggcattg    12540
tccttttcaa cccagacata aaagattaa aagagaacat agatgctgtt attattcagt    12600
gtactcattt gtatttggta gataacggat ccggcaatgt tgatgaagta aaagggttac    12660
tgaatcaata caatcaatca aagatttcta ttctgtggaa cagggaaaat cagggaattg    12720
ctaaggcatt aaatcaactt actagtgcag cacaaaaagg gggatttgat tggattctta    12780
cattggatca ggattcagtt gtcccgtcta atatcgttgg agaatttgaa aaatatataa    12840
ataattctag tgtaggaatt ctttgcccga ttatttgcga tagaaataaa ggtgaagaaa    12900
ttaaaataaa tgaagactgt acggaaatag atgaatgcat tacatctggc tctcttttga    12960
atatcaaggc atggagtgaa attggtggtt ttgatgagag gatgtttatc gatggcgttg    13020
attttgatat ttgctatcga ttaagacaaa ggggctataa aatctactgc atccatagtt    13080
tggtgttatt gcatgagatt ggacatattg aatatcatcg tttccttttc tggaaagtac    13140
ttgttatgaa ccattcggcg tttcgcaaat attatatagc tagaaatatt atttatactg    13200
ccaagaaaag aagaagtacg ctgctggttg taaaaggact attgcaagaa attaaaatga    13260
ttggcattgt aattttttat gaagaagaca agttaaataa aatcaggtgc atctgtagag    13320
gaatatatga cggctttaag ggaaaggttg gtgaatgatt atggttgcat tagaaggctt    13380
tattgtagca tattcgttca ttaatctcat attaatgatt aaaaagtaca aaagatttca    13440
tagtatatat ccggttatag ctgttttttga cttagttatg gtagttccac ttttttctaga   13500
gatgtatttt ggcatcccag ataccaag ggatgtatat atgaatttttg ttcgagctat    13560
ggaggatcaa actacattac taatatactg cttatttgtt cttctggctc agttgatgtt    13620
tacatatgaa ttaagaagaa tcaagagatt agatcgaagc gtaacaagaa ctaacgatat    13680
acaagagttt ctgctgtttta ttcaagattt caaatatcgt aagatagtta tagaaatatg    13740
ttacattatt gttgcggcaa gtgtgttttc tgttatagtt gcacctaatc caatgtacta    13800
tttgacattc cgaaatgttc atattcaggt atcagattca attgctagat actcggagca    13860
tgttattttg ccactatttg atttacttgt tggtgcgata atcgccttga agttatttga    13920
ttctaaaaat aaaattggtg gagttatttt taggataatc ttaatagttt tttttacagt    13980
ggtaaatgga aaacgagcat atctgatgat aataattggg gtgttctttt tgattgatct    14040
tcttaagcaa ggttcactaa aaaagattgc tccaaaatat gtgtttttat ttggtatggt    14100
tgcggtttat ttttatgcat atatgtatat aacagataaa attagttata atagtgattg    14160
gtattacgag atgcaggagt atattttccg ctcaatgcat gtcagattct ctatatatgc    14220
aacgcttcat cctgaaaaaa ttcatatttt ggattatccg ggacaatcga tgttatatag    14280
tttgtttttc tttatcccaa gagcaatatg gataagtaag ccgtatccat acattgatta    14340
ttatatgcgt ggagtattgg ggttatcttc attaagcaat gtgacatatc atatgccagc    14400
ttcttattat ccagagtttg tttcaaactt tggaattttg ggtctggctc tttcattaat    14460
atttacaata tggattatga gatattttga taaagaaaa acagcatgca aactattggg    14520
aactgcattg atagcattac ttaatgtcta ttattcaat gatttgctta agattgtggc    14580
aatgttatt ctctatttat gtatcactga aaagtataga tttgtgatag aaggagatg    14640
```

```
atttggaatg aagtataaat acaaaaaaca actgaccaaa attaagcgga tatttcagaa    14700
cccaggggac tttaaatatc ttaacgtgaa caaaaaggtt aagcaatctg gaatgctcct    14760
tgttattcat gaatcacaag aattaggtgc aagtatttta gcattgcata ttgctgagga    14820
acttaagcat cagggagtag atgtctatat tgtctcaagg caatttggcg tgatgaatga    14880
aaaatataat aaagttgcac cccttcagat tgcactgaac acaaaatcat atgaggtaat    14940
atgccgtaat ctttataaaa aaggctatag aaaagcatta atcattacag cttcaaatgg    15000
agatctagtg gaaattacaa aaaaatgtgg ttttaaagtg gtatctatga ttcatgaatt    15060
agagcaagtt attgagatgc ttcatttgga agatgcaaca agagatatgc tggtgtactc    15120
tgataaaatt ttgttttcaa ctacaattgc aaaaaatcag attttaagtc tctgtaaagt    15180
ttgtgacagt cagaagatat ctataaagcc gcaaggaacg tatttgaaaa agccctcatc    15240
ggaagagata aaaagacaaa gagagaagat tgcagaagcg tatcccgttt tagactgtgg    15300
caaaaaagtg atagcaggcg taggcaacac aacgagagaa aagggattcg acattttcct    15360
tcagacagca gcattaatac cggaatgtga atttatttgg gctggaaaga aggaaaatta    15420
ctacgatgag gcaattgaga aaaacggaaa tccatccaat tttattttc ttggttcact     15480 taatgccgag caattgtctg ggtatattc tcttgctgat atatacttaa tgtgttctcg     15540
atttgatacg ttgccatcaa ctattttaga agcgttactg tttggtactc ctgttatagg    15600
ggcaaaaaat tcaggtggaa ttgtggacat tatagattca gataatggat ttttaacaga    15660
aacggctgat agtaagcagt ttgcagaggc tataaaggta ggccttacta ggaattataa    15720
aattgaagag atagacggat catttgcaga atatgtggca tatgtgcttt cgttatatga    15780
ggatgaataa tgctgataac agaagataaa tattttattt ttgataaacc aagaaatgaa    15840
aattttgtat ataagacaaa atattgcata acagttatgc aatgcattgg atataaagtg    15900
ttgaagacta ttttcgtaa aaaagcgagc gatgataaaa aatattatgt ttcaatttgt     15960
ggtattttta aagatgaagc tttctatttg aaagaatgga tagagtacca taaaaaggct    16020
ggagtagatc atattta                                                   16037
```

<210> SEQ ID NO 4
<211> LENGTH: 2800
<212> TYPE: DNA
<213> ORGANISM: Streptococcus thermophilus

<400> SEQUENCE: 4

```
tgaacacacg ggagaattag agagaaatac catccaatga ggatgtgtag atagatataa      60
aaatgaggaa tgaacccagt aagagtggag gagtacatta tggaaaaatt tgattattta    120
gtagtaggtt ctggccttta cggggcgatt tttgcacatg aagccaagaa tcatggaaaa    180
tctgttttag tagtagataa gtgtcctaac attgcgggaa atatctatac caaaaacatt    240
gagggtatca atgtccataa atatggagcg catattttcc acactaacaa caaaaaggtc    300
tggaactaca ttacacagtt tgctgagttc aaccgcttca ccaactcccc cgtggccaac    360
tacaaaggcg agctgtattc gctgcctttc aacatgtata catttaataa aatgtggggc    420
gtcgtgacgc cggaggaagc tgccaccaaa atcgcggagc aacgcaagga aattactcat    480
gagcctcaga atctcgaaga gcaggccatt tctcttgtcg gccgtgatat ctacgagaaa    540
cttattaagg gctacactga gaagcagtgg gggcgcgatt gtaaagagtt gccgtccttt    600
attattaagc gtccttccgg tcgcctgact tttgataaca actacttcaa tgcgctttat    660
cagggtatcc ctgtcggtgg ttataccaag atgattgcta atctgctgga tggcattgag    720
```

```
gttcgtttga atacagacta tctggcgaac aaggtagagt tggatgcatt ggctgacaag      780
gttgtataca ctggaccgat tgatgcttac tttgactatc agttgggtac attggaatac      840
cgatctgttc gctttgaaac ggaaacattg acaagccta attttcaggg taacgcagca       900
gtgaattata ccgaccgtga actccgtgg actcgcatca ttgagcataa atggtttgag       960
tttggcaagg atgaaaatgg caatgatctg ccaaagacta tcatcagccg tgagtacagc     1020
agtgagtgga agccgggaga tgagccgtat tatccggtca acgatgctaa aatagcttg      1080 ctttattctg agtataagaa gctggcagat gcagaagaaa aagtaatctt cggcggtcgt     1140
cttggcgagt ataagtatta tgatatggac caggtaattg cagctgtgtt ggataaatgc     1200
aagaaggagc tgggagaata aaatggcaaa gaaaaagatt ttaatggtct gtgaagcttt     1260
tggaggtgga gtatttacct atgtatctca actctgcaac gatatggtgg atgattttga     1320
cgtttatctt gcatattccc tcagaccgca gaccctaag aattacaaag attttctgga      1380
tcagagagtg catttgattg aaatgcaaaa tgtcggagtt aagggactaa caaacttaaa     1440
gagtgacatt gcagcaatta aggaattgcg tcagattgaa aaagatgttc agccagatgt     1500
gattcacctg cattcttcgg ttgcaggtgg tttaggtaga cttgcatata cggaaaaaa      1560 taatactgtt gtgtacacac ctcatgggta tgcacatatt cttatgggtc ggggaagaa      1620 gagaaaagtc tataagtttg cagaaaaggt tctcggaaat cgagcactta cacttacctg     1680
ttgcgaaagt gaagatgaag aagcaaagaa attctccaag agaacagctt atgttgaaac     1740
gggtgtgaat cttgcagacc tttcggcatc ccttgacggt attaagcctg taaaaaatga     1800
taagttcaca gttttacgc ttggtcgcgc ctgcgttcag aaacagccac agctttttaa      1860
tagaattgct gaactagtac cagatgcaag attttatttgg attggtaacg agaacttga     1920 aaatgagtta actgctccaa atattgaagt gacgggatgg aaacctcgta aggaagcttt     1980
ggcaatggcc aaaggtgcag atgcatttat tttgtgcagt cttggtgaag ctattgcaat     2040 gagcctatt gagaatatgt acattaaaaa gctgattctc gttagcaata caatgggaaa      2100
taagagtgtt atcaatgatg gcatcaatgg atatgtctgt gataaggcgg aggagtatgc     2160
tgaacatata aaagcggcta tgaaggagtt tcctaaagaa cttcctgaaa gagcatatca     2220
ggatgtcctt gagatttata atactgatgc catgaagaag aagtatattg agttttataa     2280
tgatgttgtg gcaggtaaat actgatgata aaaaatatgg actatttagt ttccgtcatt     2340
gttcccatat acaaagtgga aaagatttg tcggattgcg ttctgagcat ttgcaatcag      2400
acctatacaa atttagagat tattcttgtt gatgatggct ctccagataa ttgtggacaa     2460
atgtgtgatg aatttgcaaa aaatgatgtc cgaataaagg ttattcataa aattaatgga    2520
gggttatcac aagctcgaaa tgctggaatg agcattatga cgggagatta tattacattt     2580
gttgatagcg atgacttttt ggaacatgaa tttattgaag aaatgttgag gataattaat     2640
aaatataatg ctcaagttgc aatttgcaaa aattctacat ttgaaaaagg cggtacactt     2700
aataatggtc atgtaggaat aagcgaacga agctttgatg cggtagaagc cataaagaac     2760
atgttatatc aaaaggattt tgatgttgca gcatggggaa                           2800

<210> SEQ ID NO 5
<211> LENGTH: 1043
<212> TYPE: DNA
<213> ORGANISM: Streptococcus thermophilus

<400> SEQUENCE: 5
aacgttgcag atgtctgcaa gaagatggat tgcaaaatga cctacatcag cacagactat      60
```

```
gtgttcgatg gtcagggtac cgagccttgg cagccggact gcaaggatta caagcctttg    120
aatgtgtacg gtcagacgaa gctggaaggt gagttggcgg ttagccagac gttggagagg    180
tatttcattg tccgcattgc atgggtattt ggtctgaatg gtaagaactt catcaagacg    240
atgctgaatg tcggcaagac acacaatact gtccgtgtgg tcaatgatca gatcggtaca    300
ccgacctata catacgattt ggctcgactg ctcgtcgata tgaatgagac tgagaagtat    360
ggctattacc atgcgaccaa cgagggtggt tatatcagct ggtacgattt aacgaaagaa    420
atttatcgtc aggtgggcta taagacagca gaggtgcgtc cggtaagtac ggaagagtat    480
gtcctgagta aagcaactcg cccgtttaac agtcgtctgg ataagagcaa gttggtagaa    540
gctggcttta ctctgcttcc gacctggcaa gatgcgctga gccgttacct gaaagaagtt    600
gagcagtaag aggagataga gaagatggga cagataaaag ttgagaaaaa tgtaggcggt    660
atcgaaggac tttgcgttat tgaacctgct gttcatggcg atgctcgtgg ctatttcatg    720
gaaacctaca acgaaaaaga tatgaaagaa gcaggcattg acatccactt cgtgcaggac    780
aatcagtcta tgtccactaa gggcgttctg cgcggtttgc atttccagaa gcagtatccg    840
cagtgcaagc tggtacgcgc catgcgtggt actgtgtttg atgttgcggt tgacctgaga    900
agtgattcta agagttacgg caagtggtat ggtgttacac tgtccgctga gaacaagaag    960
cagttcctca ttccagaggg atttgcgcac ggtttcctgg ttctgagcga tgaggcagag   1020
ttctgctata aggtcaacga ctt                                           1043

<210> SEQ ID NO 6
<211> LENGTH: 91
<212> TYPE: DNA
<213> ORGANISM: Streptococcus thermophilus

<400> SEQUENCE: 6
tcccagttgg agatatccaa atgaattcag agcaagcact tggatttgtt cgtgaacgct    60
atagtttaga tggcggagat aatgatcgtg g                                    91

<210> SEQ ID NO 7
<211> LENGTH: 91
<212> TYPE: DNA
<213> ORGANISM: Streptococcus thermophilus

<400> SEQUENCE: 7
tcccagttgg agatatccaa atgaattcag agcaagcact tggatttgtt cgtgaacgct    60
atagtttaga tggcggagat aatgatcgtg g                                    91

<210> SEQ ID NO 8
<211> LENGTH: 91
<212> TYPE: DNA
<213> ORGANISM: Streptococcus thermophilus

<400> SEQUENCE: 8
tcccagttgg agatatccaa atgaattcag agcaagcact tggatttgtt cgtgaacgct    60
atagtttaga tggcggagat aatgatcgtg g                                    91

<210> SEQ ID NO 9
<211> LENGTH: 69
<212> TYPE: DNA
<213> ORGANISM: Streptococcus thermophilus

<400> SEQUENCE: 9
gaattcagag caagcacttg gatttgttcg tgaacgctat agtttagatg gcggagataa    60
```

```
tgaccgtgg                                                                69

<210> SEQ ID NO 10
<211> LENGTH: 91
<212> TYPE: DNA
<213> ORGANISM: Streptococcus thermophilus

<400> SEQUENCE: 10
tcccggttgg agatatccaa atgaattcag agcaagcact tggatttgtt cgtgaacgct      60
atagtttaga tggcggagat aatgatcgtg g                                     91

<210> SEQ ID NO 11
<211> LENGTH: 91
<212> TYPE: DNA
<213> ORGANISM: Streptococcus thermophilus

<400> SEQUENCE: 11
tcccagttgg agatatccaa atgaattcag agcaagcact tggatttgtt cgtgaacgct      60
atagtttaga tggcggagat aatgatcgtg g                                     91

<210> SEQ ID NO 12
<211> LENGTH: 91
<212> TYPE: DNA
<213> ORGANISM: Streptococcus thermophilus

<400> SEQUENCE: 12
tcccagttgg agatatccaa atgaattcag agcaagcact tggatttgtt cgtgaacgct      60
atagtttaga tggcggagat aatgaccgtg g                                     91

<210> SEQ ID NO 13
<211> LENGTH: 91
<212> TYPE: DNA
<213> ORGANISM: Streptococcus thermophilus

<400> SEQUENCE: 13
tcccggttgg agatatccaa atgaattcag agcaagcact tggatttgtt cgtgaacgct      60
atagtttaaa tggcggagat aatgatcgtg g                                     91

<210> SEQ ID NO 14
<211> LENGTH: 91
<212> TYPE: DNA
<213> ORGANISM: Streptococcus thermophilus

<400> SEQUENCE: 14
tcccagttgg agatatccaa atgaattcag agcaagcact tggatttgtt cgtgaacgct      60
atagtttaga tggcggagat aatgaccgtg g                                     91

<210> SEQ ID NO 15
<211> LENGTH: 91
<212> TYPE: DNA
<213> ORGANISM: Streptococcus thermophilus

<400> SEQUENCE: 15
tcccggttgg agatatccaa atgaattcag agcaagcact tggatttgtt cgtgaacgct      60
ataatttaga tggcggagat aatgaccgtg g                                     91

<210> SEQ ID NO 16
<211> LENGTH: 91
<212> TYPE: DNA
<213> ORGANISM: Streptococcus thermophilus
```

```
<400> SEQUENCE: 16
tcccggttgg agatatccaa atgaattcag agcaagcact tggatttgtt cgtgaacgct    60
ataatttaga tggcggagat aatgaccgtg g                                   91

<210> SEQ ID NO 17
<211> LENGTH: 91
<212> TYPE: DNA
<213> ORGANISM: Streptococcus thermophilus

<400> SEQUENCE: 17
tcccagttgg agatatccaa atgaattcag agcaagcact tggatttgtt cgtgaacgct    60
atagtttaga tggcggagat aatgatcgtg g                                   91

<210> SEQ ID NO 18
<211> LENGTH: 91
<212> TYPE: DNA
<213> ORGANISM: Streptococcus thermophilus

<400> SEQUENCE: 18
tcccagttgg agatatccaa atgaattcag agcaagcact tggatttgtt cgtgaacgct    60
atagtttaga tggcggagat aatgaccgtg g                                   91

<210> SEQ ID NO 19
<211> LENGTH: 91
<212> TYPE: DNA
<213> ORGANISM: Streptococcus thermophilus

<400> SEQUENCE: 19
tcccagttgg agatatccaa atgaattcag agcaagcact tggatttgtt cgtgaacgct    60
atagtttaga tggcggagat aatgatcgtg g                                   91

<210> SEQ ID NO 20
<211> LENGTH: 91
<212> TYPE: DNA
<213> ORGANISM: Streptococcus thermophilus

<400> SEQUENCE: 20
tcccagttgg agatatccaa atgaattcag agcaagcact tggatttgtt cgtgaacgct    60
atagtttaga tggcggagat aatgaccgtg g                                   91

<210> SEQ ID NO 21
<211> LENGTH: 91
<212> TYPE: DNA
<213> ORGANISM: Streptococcus thermophilus

<400> SEQUENCE: 21
tcccagttgg agatatccaa atgaattcag agcaagcact tggatttgtt cgtgaacgct    60
atagtttaga tggcggagat aatgaccgtg g                                   91

<210> SEQ ID NO 22
<211> LENGTH: 91
<212> TYPE: DNA
<213> ORGANISM: Streptococcus thermophilus

<400> SEQUENCE: 22
tcccagttgg agatatccaa atgaattcag agcaagcact tggatttgtt cgtgaacgct    60
atagtttaga tggcggagat aatgaccgtg g                                   91
```

```
<210> SEQ ID NO 23
<211> LENGTH: 91
<212> TYPE: DNA
<213> ORGANISM: Streptococcus thermophilus

<400> SEQUENCE: 23
tcccggttgg agatatccaa atgaattcag agcaagcact tggatttgtt cgtgaacgct    60
ataatttaga tggcggagat aatgaccgtg g                                   91

<210> SEQ ID NO 24
<211> LENGTH: 91
<212> TYPE: DNA
<213> ORGANISM: Streptococcus thermophilus

<400> SEQUENCE: 24
tcccggttgg agatatccaa atgaattcag agcaagcact tggatttgtt cgtgaacgct    60
ataatttaga tggcggagat aatgaccgtg g                                   91

<210> SEQ ID NO 25
<211> LENGTH: 91
<212> TYPE: DNA
<213> ORGANISM: Streptococcus thermophilus

<400> SEQUENCE: 25
tcccggttgg agatatccaa atgaattcag agcaagcact tggatttgtt cgtgaacgct    60
ataatttaga tggcggagat aatgaccgtg g                                   91

<210> SEQ ID NO 26
<211> LENGTH: 91
<212> TYPE: DNA
<213> ORGANISM: Streptococcus thermophilus

<400> SEQUENCE: 26
tcccggttgg agatatccaa atgaattcag agcaagcact tggatttgtt cgtgaacgct    60
ataatttaga tggcggagat aatgaccgtg g                                   91

<210> SEQ ID NO 27
<211> LENGTH: 91
<212> TYPE: DNA
<213> ORGANISM: Streptococcus thermophilus

<400> SEQUENCE: 27
tcccggttgg agatatccaa atgaattcag agcaagcact tggatttgtt cgtgaacgct    60
ataatttaga tggcggagat aatgaccgtg g                                   91

<210> SEQ ID NO 28
<211> LENGTH: 91
<212> TYPE: DNA
<213> ORGANISM: Streptococcus thermophilus

<400> SEQUENCE: 28
tcccggttgg agatatccaa atgaattcag agcaagcact tggatttgtt cgtgaacgct    60
ataatttaga tggcggagat aatgaccgtg g                                   91

<210> SEQ ID NO 29
<211> LENGTH: 91
<212> TYPE: DNA
<213> ORGANISM: Streptococcus thermophilus

<400> SEQUENCE: 29
tcccggttgg agatatccaa atgaattcag agcaagcact tggatttgtt cgtgaacgct    60
```
ataatttaga tggcggagat aatgaccgtg g                                          91

<210> SEQ ID NO 30
<211> LENGTH: 91
<212> TYPE: DNA
<213> ORGANISM: Streptococcus thermophilus

<400> SEQUENCE: 30
aagtggttct cagttcttag gggtcgtcct taataaagtt gacatgacag ttgataaata         60
tggatcgtat ggttcttacg gatcatatgg c                                          91

<210> SEQ ID NO 31
<211> LENGTH: 91
<212> TYPE: DNA
<213> ORGANISM: Streptococcus thermophilus

<400> SEQUENCE: 31
aagtggttct cagttcttag gggtcgtcct taataaagtt gacatgacag ttgataaata         60
tggatcgtat ggttcttacg gatcatatgg c                                          91

<210> SEQ ID NO 32
<211> LENGTH: 91
<212> TYPE: DNA
<213> ORGANISM: Streptococcus thermophilus

<400> SEQUENCE: 32
aagtggttct cagttcttag gggtcgtcct taataaagtt gacatgacag ttgataaata         60
tggatcgtat ggttcttacg gatcatatgg c                                          91

<210> SEQ ID NO 33
<211> LENGTH: 91
<212> TYPE: DNA
<213> ORGANISM: Streptococcus thermophilus

<400> SEQUENCE: 33
aagtggttct cagttcttag gggtcgtcct taataaagtt gacatgacag ttgataaata         60
tggatcgtat ggttcttacg gatcatatgg c                                          91

<210> SEQ ID NO 34
<211> LENGTH: 91
<212> TYPE: DNA
<213> ORGANISM: Streptococcus thermophilus

<400> SEQUENCE: 34
aagtggttct cagttcttag gtgtcgtcct taataaagtt gacatgacag ttgctaaata         60
tggatcatat ggttcttacg gatcatatgg c                                          91

<210> SEQ ID NO 35
<211> LENGTH: 90
<212> TYPE: DNA
<213> ORGANISM: Streptococcus thermophilus

<400> SEQUENCE: 35
aagtggttct cagttcttag gtgtcgtcct taataaagtt gacatgacag ttgataaata         60
tggatcatat ggttcttacg gatcatatgg                                            90

<210> SEQ ID NO 36
<211> LENGTH: 91
<212> TYPE: DNA
<213> ORGANISM: Streptococcus thermophilus

```
<400> SEQUENCE: 36
aagtggttct cagttcttag gggtcgtcct taataaagtt gacatgacag ttgataaata      60
tggatcgtat ggttcttacg gatcatatgg c                                    91

<210> SEQ ID NO 37
<211> LENGTH: 91
<212> TYPE: DNA
<213> ORGANISM: Streptococcus thermophilus

<400> SEQUENCE: 37
aagtggttct cagttcttag gggtcgtcct taataaagtt gacatgacag ttgataaata      60
tggattttat ggttcttacg gtttatatgg c                                    91

<210> SEQ ID NO 38
<211> LENGTH: 91
<212> TYPE: DNA
<213> ORGANISM: Streptococcus thermophilus

<400> SEQUENCE: 38
aagtggttct cagttcttag gggtcgtcct taataaagtt gacatgacag ttgataaata      60
tggatcgtat ggttcttacg gatcatatgg c                                    91

<210> SEQ ID NO 39
<211> LENGTH: 91
<212> TYPE: DNA
<213> ORGANISM: Streptococcus thermophilus

<400> SEQUENCE: 39
aagtggttct cagttcttag gtgtcgtcct taataaagtt gacatgacag ttgataaata      60
tggatcgtat ggttcttacg gatcatatgg c                                    91

<210> SEQ ID NO 40
<211> LENGTH: 91
<212> TYPE: DNA
<213> ORGANISM: Streptococcus thermophilus

<400> SEQUENCE: 40
aagtggttct cagttcttag gggtcgtcct taataaagtt gacatgacag ttgataaata      60
tggattttat ggttcttacg gatcatatgg c                                    91

<210> SEQ ID NO 41
<211> LENGTH: 91
<212> TYPE: DNA
<213> ORGANISM: Streptococcus thermophilus

<400> SEQUENCE: 41
aagtggttct cagttcttag gggtcgtcct taataaagtt gacatgacag ttgataaata      60
tggatcatat ggttcttacg gatcatatgg c                                    91

<210> SEQ ID NO 42
<211> LENGTH: 91
<212> TYPE: DNA
<213> ORGANISM: Streptococcus thermophilus

<400> SEQUENCE: 42
aagtggttct cagttcttag gtgtcgtcct taataaagtt gacatgacag ttgataaata      60
tggatcatat ggttcttacg gatcatatgg t                                    91
```

```
<210> SEQ ID NO 43
<211> LENGTH: 90
<212> TYPE: DNA
<213> ORGANISM: Streptococcus thermophilus

<400> SEQUENCE: 43
aagtggttct cagttcttag gtgtcgtcct taataaagtt gacatgacag ttgataaata    60
tggatcatat ggttcttacg gatcatatgg                                    90

<210> SEQ ID NO 44
<211> LENGTH: 91
<212> TYPE: DNA
<213> ORGANISM: Streptococcus thermophilus

<400> SEQUENCE: 44
aagtggttct cagttcttag gtgtcgtcct taataaagtt gacatgacag ttgataaata    60
tggatcatat ggttcttacg gatcatatgg t                                  91

<210> SEQ ID NO 45
<211> LENGTH: 90
<212> TYPE: DNA
<213> ORGANISM: Streptococcus thermophilus

<400> SEQUENCE: 45
aagtggttct cagttcttag gggtcgtcct taataaagtt gacatgacag ttgataaata    60
tggatcgtat ggttcttacg gatcatatgg                                    90

<210> SEQ ID NO 46
<211> LENGTH: 91
<212> TYPE: DNA
<213> ORGANISM: Streptococcus thermophilus

<400> SEQUENCE: 46
aagtggttct cagttcttag gtgtcgtcct taataaagtt gacatgacag ttgataaata    60
tggatcatat ggttcttacg gatcatatgg c                                  91

<210> SEQ ID NO 47
<211> LENGTH: 91
<212> TYPE: DNA
<213> ORGANISM: Streptococcus thermophilus

<400> SEQUENCE: 47
aagtggttct cagttcttag gggtcgtcct taataaagtt gacatgacag ttgataaata    60
tggatcgtat ggttcttacg gatcatatgg a                                  91

<210> SEQ ID NO 48
<211> LENGTH: 91
<212> TYPE: DNA
<213> ORGANISM: Streptococcus thermophilus

<400> SEQUENCE: 48
aagtggttct cagttcttag gggtcgtcct taataaagtt gacatgacag ttgataaata    60
tggatcgtat ggttcttacg gatcatatgg a                                  91

<210> SEQ ID NO 49
<211> LENGTH: 91
<212> TYPE: DNA
<213> ORGANISM: Streptococcus thermophilus

<400> SEQUENCE: 49
aagtggttct cagttcttag gggtcgtcct taataaagtt gacatgacag ttgataaata    60
```

```
tggatttat ggttcttacg gatcatatgg c                              91

<210> SEQ ID NO 50
<211> LENGTH: 91
<212> TYPE: DNA
<213> ORGANISM: Streptococcus thermophilus

<400> SEQUENCE: 50
aagtggttct cagttcttag gggtcgtcct taataaagtt gacatgacag ttgataaata    60 tggatttat ggttcttacg gatcatatgg c                              91

<210> SEQ ID NO 51
<211> LENGTH: 91
<212> TYPE: DNA
<213> ORGANISM: Streptococcus thermophilus

<400> SEQUENCE: 51
aagtggttct cagttcttag gggtcgtcct taataaagtt gacatgacag ttgataaata    60 tggatttat ggttcttacg gatcatatgg c                              91

<210> SEQ ID NO 52
<211> LENGTH: 91
<212> TYPE: DNA
<213> ORGANISM: Streptococcus thermophilus

<400> SEQUENCE: 52
aagtggttct cagttcttag gggtcgtcct taataaagtt gacatgacag ttgataaata    60 tggatttat ggttcttacg gatcatatgg c                              91

<210> SEQ ID NO 53
<211> LENGTH: 91
<212> TYPE: DNA
<213> ORGANISM: Streptococcus thermophilus

<400> SEQUENCE: 53
aagtggttct cagttcttag gggtcgtcct taataaagtt gacatgacag ttgataaata    60 tggatttat ggttcttacg gatcatatgg c                              91

<210> SEQ ID NO 54
<211> LENGTH: 91
<212> TYPE: DNA
<213> ORGANISM: Streptococcus thermophilus

<400> SEQUENCE: 54
aagtggttct cagttcttag gtgtcgtcct taataaagtt gacatgacag ttgataaata    60
tggatcatac ggttcgtatg gatcatacgg t                              91

<210> SEQ ID NO 55
<211> LENGTH: 90
<212> TYPE: DNA
<213> ORGANISM: Streptococcus thermophilus

<400> SEQUENCE: 55
aagtggttct cagttcttag gggtcgtcct taataaagtt gacatgacag ttgataaata    60
tggatcatat ggttcttacg gatcataggc                                90

<210> SEQ ID NO 56
<211> LENGTH: 91
<212> TYPE: DNA
<213> ORGANISM: Streptococcus thermophilus
```

```
<400> SEQUENCE: 56
aagtggttct cagttcttag gggtcgtcct taataaagtt gacatgacag ttgataaata    60
tggattttat ggttcttacg gatcatatgg c                                   91

<210> SEQ ID NO 57
<211> LENGTH: 91
<212> TYPE: DNA
<213> ORGANISM: Streptococcus thermophilus

<400> SEQUENCE: 57
aagtggttct cagttcttag gggtcgtcct tattaaagtt gacatgacag ttgataaata    60
tggatcgtat ggttcttacg gatcatatgg a                                   91

<210> SEQ ID NO 58
<211> LENGTH: 91
<212> TYPE: DNA
<213> ORGANISM: Streptococcus thermophilus

<400> SEQUENCE: 58
aagtggttct cagttcttag gtgtcgtcct taataaagtt gacatgacag ttgataaata    60
tggatcatat ggttcttacg gatcatatgg t                                   91

<210> SEQ ID NO 59
<211> LENGTH: 91
<212> TYPE: DNA
<213> ORGANISM: Streptococcus thermophilus

<400> SEQUENCE: 59
aagtggttct cagttcttag gtgtcgtcct taataaagtt gacatgacag ttgataaata    60
tggatcatat ggttcttacg gatcatatgg t                                   91

<210> SEQ ID NO 60
<211> LENGTH: 91
<212> TYPE: DNA
<213> ORGANISM: Streptococcus thermophilus

<400> SEQUENCE: 60
aagtggttct cagttcttag gtgtcgtcct taataaagtt gacatgacag ttgataaata    60
tggatcatat ggttcttacg gatcatatgg t                                   91

<210> SEQ ID NO 61
<211> LENGTH: 91
<212> TYPE: DNA
<213> ORGANISM: Streptococcus thermophilus

<400> SEQUENCE: 61
aagtggttct cagttcttag gtgtcgtcct taataaagtt gacatgacag ttgatagata    60
tggatcatat ggttcttacg gatcatatgg t                                   91
```

GENETIC CLUSTER OF STRAINS OF STREPTOCOCCUS THERMOPHILUS HAVING APPROPRIATE ACIDIFYING AND TEXTURIZING PROPERTIES FOR DAIRY FERMENTATIONS

The present application is filed pursuant to 35 U.S.C. 371 as a U.S. National Phase application of International Patent Application No. pct/ep07/60463, which was filed Oct. 2, 2007, claiming the benefit of priority to French Patent Application No. 0608657, which was filed on Oct. 3, 2006. The entire text of the aforementioned applications is incorporated herein by reference in its entirety.

The invention relates to a genetic cluster of strains of *Streptococcus thermophilus* (*S. thermophilus*) having appropriate acidifying and texturizing properties for dairy fermentations.

Bacteriophages are viruses capable of attacking bacteria. During se viral attacks, the bacteriophages infect the bacterial culture, and multiply in order to finally destroy this culture. The technological impact on the milk processing industry (production of cheese, yoghurt, fermented milk) of these bacteriophages is significant since they can cause a complete cessation of fermentation and therefore prevent the production of these milk-derived products.

One way of combating the problems linked to the infection of the fermentations by bacteriophages is the use of strains having appropriate sensitivity spectra to the phages. In particular, producers of dairy ferments have developed strategies to combat the bacteriophages by constructing ferments constituted by several strains having distinct lysotypes, and using several of these ferments in rotation. It is clear that in order to be able to adopt this strategy it is important to possess a diversity of strains having the same functionalities (such as for example acidification, thickening power, flavouring etc.) but distinct lysotypes.

*S. thermophilus* are used extensively alone or in combination with other bacteria for the production of fermented food products. They are included in particular in the formulation of the ferments used for producing yoghurts. Strains of *S. thermophilus* are expected to participate in the formation of lactic curd by acidification of milk and in the development of the texture of the fermented product. A distinction generally drawn between 4 groups of *S. thermophilus* based on these functional properties: 1) non-texturizing and non-acidifying strains, 2) the non-texturizing and acidifying strains, 3) the texturizing and non-acidifying strains, and 4) the texturizing and acidify strains. A texturizing strain is a strain making, it possible to obtain fermented milks the gels of which can be described by their rheological properties.

Hitherto only four strains of *S. thermophilus* corresponding criteria of acidifying and texturizing strains have been described in the literature: Sfi39, CNCM I-2423, CNCM I-2426 and the strain CNCM I-2980 described in the Application WO2004/085607.

The rarity of such strains (rapid acidification and texturizing) makes it difficult to combat the bacteriophages during the fermentation of the milk. In fact, ideally, the fight against the bacteriophages would involve the combination in the same ferment of strains having similar technological properties but distinct lysotypes, then the use of ferments of this type in rotation. The ferments used in rotation should also have distinct lysotypes but similar technological properties. In the case of the texturizing and rapidly acidifying ferments, this approach is difficult in view of the small number of strains having these functional qualities.

Thus one of the problems which the invention proposes to resolve is to provide novel strains of *S. thermophilus* which have a lysotype distinct from the strains currently used, in particular strains which are acidifying and texturizing.

For this purpose, the invention relates to the strains of *S. thermophilus* in a genetic cluster which have a lysotype distinct from that of the acidifying and texturizing strains of *S. thermophilus* currently used. Within this cluster novel acidifying and texturizing strains have been identified.

The invention also describes a method making it possible to predict a strain's membership of a family of strains having identical or related lysotypes. This method analyzes the restriction polymorphism of the epsA-B-C-D region of the genome of *S. thermophilus*.

By the epsA-B-C-D region is meant the region of the chromosome of *S. thermophilus* overlapping the epsA to epsD genes of the eps locus. The DNA fragment corresponding to this region, called the epsAD fragment, can be obtained by PCR reaction on the chromosomic DNA or *S. thermophilus* oligonucleotides of SEQ ID No1 and SEQ ID No2 as primers.

A subject of the present invention is a strain of *Streptococcus thermophilus* the epsAD fragment of which, after digestion by the restriction enzymes Mn/I, FokI and HindIII, has a restriction profile characterized by DNA fragments of $344\pm2$ base pairs (bp), $341\pm2$ bp, $305\pm2$ bp, $299\pm2$ bp, $277\pm2$ bp, $210\pm2$ bp, $160\pm2$ bp, $142\pm2$ bp, $100\pm2$ bp, $79\pm2$ bp, $75\pm2$ bp, $66\pm2$ bp, $42\pm2$ bp, $23\pm2$ bp and $9\pm2$ bp.

The restriction profile of the epsAD fragment is determined by standard sequencing of the epsAD fragment followed by in silico determination of the restriction profile.

Typically the sequencing can be carried out with the CEQ8000 equipment (Beckman) and the in silico determination of the restriction profile can be carried out starting from the sequence of the epsAD fragment using the NEBcutter V2.0 tool accessible on the internet.

Typically a strain according to the invention comprises a nucleotide sequence having at least 80%, preferentially at least 90%, at least 95% or at least 97% and still more preferentially 100% identity with the nucleotide sequence of SEQ ID No4.

Typically a strain according to the invention comprises a nucleotide sequence having at least 80%, preferentially at least 90%, at least 95% or at least 97% and still more preferentially 100% identity with the nucleotide sequence of SEQ ID No5.

In order to calculate the percentage identity, a person skilled in the art will for example use the "BLAST 2 Sequences" tool (Tatusova & Madden, 1999) with the default parameters of the "blastn" program (for alignment of nucleotide sequences) or of the "blastp" program (for alignment of protein sequences). The percentage similarity between two protein sequences is calculated using the BLOSUM62 matrix.

Preferentially the strain according to the invention is texturizing. Preferentially the strain according to the invention acidifies rapidly. Still more preferentially the strain according to the invention is texturizing and acidifies rapidly.

By texturizing strain of *Streptococcus thermophilus* is meant a strain which produces fermented milks having, under the conditions described in the example, a viscosity greater than approximately 35 Pa·s, a thixotropic area of less than approximately 2000 Pa/s and/or a yield point of less than approximately 14 Pa.

By rapidly acidifying strain is meant a strain which under the conditions described in the example, a Vm of less than −0.0100 upH/min.

Preferentially, a strain according to the invention is the strain of *Streptococcus thermophilus* deposited on 14 Jun.

2006 at the Collection Nationale de Cultures de Microorganismes under no. CNCM I-3617 or a mutant strain which can be obtained from the latter.

Typically in order to obtain such mutant strains, a person skilled in the art can use the usual mutagenesis techniques such as UV irradiation or exposure to mutagenic chemical products (ethyl-methane-sulphonate, nitrosoguanidine, nitrous acid etc.).

Preferentially, a subject of the invention is the strain of *Streptococcus thermophilus* deposited on 14 Jun. 2006 in the name of Danisco France SAS, 20 rue de Brunel, 75017 Paris at the Collection Nationale de Cultures de Microorganismes under no. CNCM I-3617.

A person skilled in the art, starting from the restriction profiles described previously and/or from the sequences of SEQ ID No4 and/or No5, can identify the strains which belong to the same genetic cluster the strain CNCM I-3617. Typically in order to do this, he can use PCR and/or hybridization and/or DNA sequencing techniques.

A subject of the invention is also a bacterial composition comprising at least one strain according to the invention. By bacterial composition is meant a mixture of different strains, in particular a ferment, or a leaven.

The mixtures of preferred strains according to the invention are mixtures of *Streptococcus thermophilus* with other *Streptococcus thermophilus*, or mixtures of *Streptococcus thermophilus* with *Lactobacillus delbrueckii* subsp. *bulgaricus*, or mixtures of *Streptococcus thermophilus* with other *Lactobacillus* and/or with *Bifidobacterium*, or mixtures of *Streptococcus thermophilus* with *Lactococcus*, or mixtures of *Streptococcus thermophilus* with other strains of lactic bacteria and/or yeasts.

A subject of the invention is also a manufacturing process for a food product, a food complement, a dietary supplement or a product with probiotic properties, comprising a stage in which a strain according to the invention is used.

Typically the food product, the food complement, the dietary supplement or the product with probiotic properties is a dairy product, a meat product, a cereal product, a drink, a foam or a powder.

Preferentially the food product, the food complement, the dietary supplement or the product with probiotic properties is a dairy product. It is for example a fermented milk, a yoghurt, a matured cream, a cheese, a fromage frais, a milk drink, a dairy product retentate, a processed cheese, a cream dessert, a cottage cheese or an infant milk. Typically the dairy product comprises milk of animal and/or plant origin.

A subject of the invention is also a food product, a food complement, a dietary supplement or a product with probiotic properties comprising at least one strain according to the invention or the bacterial composition described previously.

The invention also describes a method for predicting the lysotype of a strain of *S. thermophilus* starting from analysis of the restriction polymorphism of the epsA-B-C-D region of its genome, comprising the following stages:
a) amplification of the epsAD fragment by PCR reaction on the chromosomic DNA of *S. thermophilus* using the oligonucleotides of SEQ ID No1 and SEQ ID No2 as primers;
b) sequencing of the epsAD fragment;
c) in silico determination of the restriction profile of the epsAD fragment after digestion by the restriction enzymes Mn/I, FokI and HindIII; and
d) comparison of the restriction profile obtained in Stage c) with the restriction profiles of the epsAD region of strains of *S. thermophilus* the lysotype which is known.

Examples of strains of *Streptococcus thermophilus* the lysotype of which is known are listed in Table 3.

The present invention is better illustrated below using the examples which follow. These examples are given only by way of illustration of the subject-matter of the invention, of which they in no way constitute a limitation.

BRIEF DESCRIPTIONS OF THE FIGURES

FIG. 1: Diagrammatic representation of the eps locus of various *Streptococcus thermophilus* having similarities in organization and sequence of the 5' region including the epsA, epsB, epsC and epsD genes. The GENBANK access numbers of the nucleotide sequences are given in parentheses.

Figure 2A:
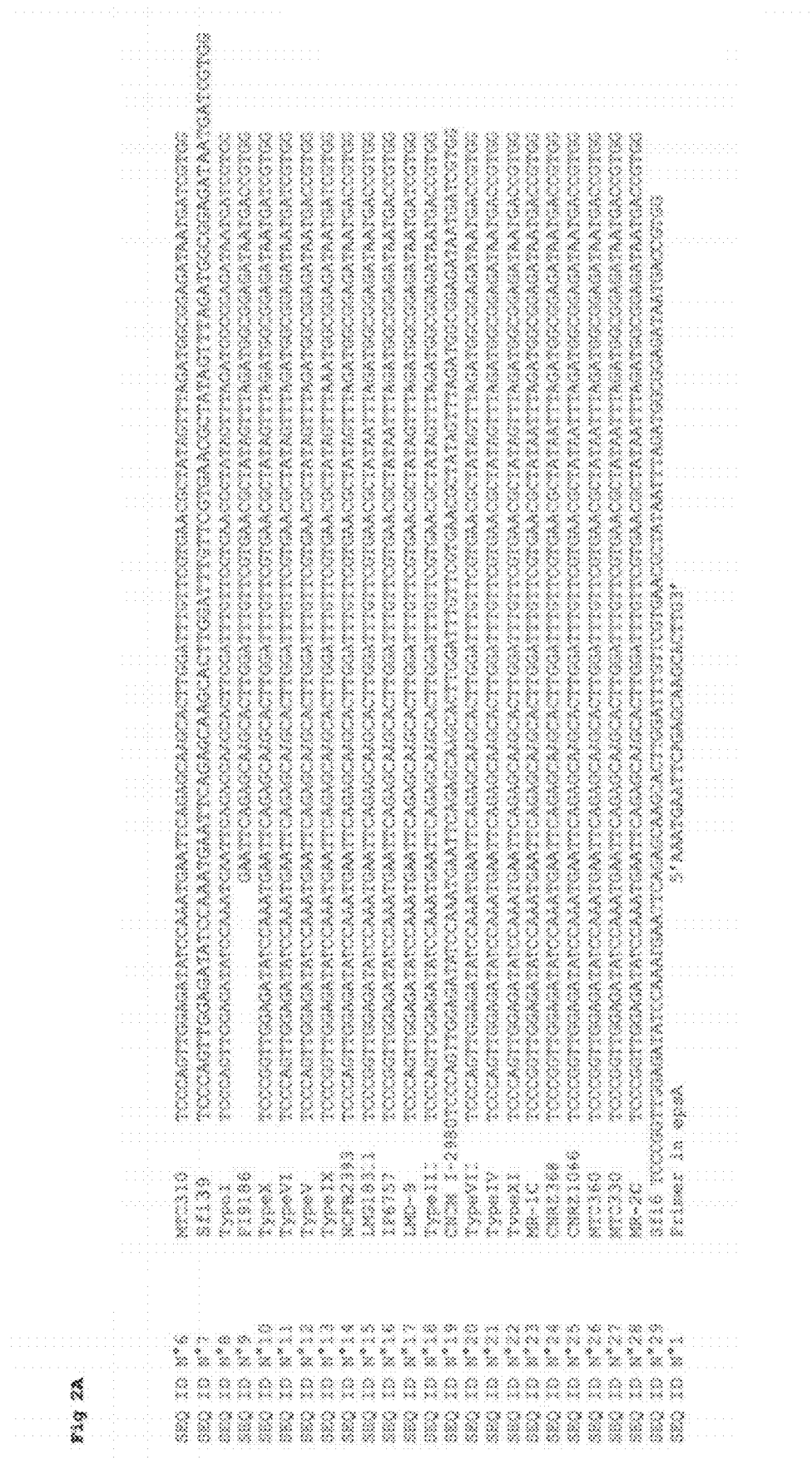

FIG. 2: Alignment of partial sequences of the epsA (A) and epsD (B)genes at the level f the regions targeted by the primers of SEQ ID NO:1 (in the epsA gene) and SEQ ID NO:2 (in the epsD gene). The sequences in the Figure are as follows SEQ ID NO:6 MTC310; SEQ ID NO: 7 Sfi39; SEQ ID NO:8 TypeI; SEQ ID NO:9 F19186; SEQ ID NO:10 TypeX; SEQ ID NO:11 TypeVI; SEQ ID NO:12 TypeV; SEQ ID NO:13 TypeIX; SEQ ID NO:14 NCDB2393; SEQ ID NO:15 LMG18311; SEQ ID NO:16 IP6757; SEQ ID NO:17 LMD-9; SEQ ID NO:18 TypeIII; SEQ ID NO:19 CNCM 12980; SEQ ID NO:20 TypeVII; SEQ ID NO:21 Type IV; SEQ ID NO:22 Type XI; SEQ ID NO:23 MR-1C; SEQ ID NO:24 CNRZ368; SEQ ID NO:25 CNRZ1065; SEQ ID NO:26 MTC360; SEQ ID NO:27 MTC330; SEQ ID NO:28 MR-2C; SEQ ID NO:29 Sfi6; SEQ ID NO:30 MTC310; SEQ ID NO: 31 Sfi39; SEQ ID NO:32 TypeI; SEQ ID NO:33 F19186; SEQ ID NO:34 TypeX; SEQ ID NO:35 TypeVI; SEQ ID NO:36 TypeV; SEQ ID NO:37 TypeIX; SEQ ID NO:38 NCDB2393; SEQ ID NO:39 LMG18311; SEQ ID NO:40 IP6757; SEQ ID NO:41 LMD-9; SEQ ID NO:42 TypeIII; SEQ ID NO:43 CNCM 12980; SEQ ID NO:44 TypeVII; SEQ ID NO:45 Type IV; SEQ ID NO:46 Type XI; SEQ ID NO:47 MR-1C; SEQ ID NO:48 CNRZ368; SEQ ID NO:49 CNRZ1065; SEQ ID NO:50 MTC360; SEQ ID NO:51 MTC330; SEQ ID NO:52 MR-2C; SEQ ID NO:53 Sfi6; SEQ ID NO:54 ST69 (AJ488593); SEQ ID NO:55 A2 (AJ488600); SEQ ID NO:56 D1 (AJ488599); SEQ ID NO:57 E1 (AJ488598); SEQ ID NO:58 I1 (AJ488597); SEQ ID NO:59 I1 (AJ488596); SEQ ID NO:60 N1 (AJ488595); and SEQ ID NO:61 Q1 (AJ488594).

Figure 3:
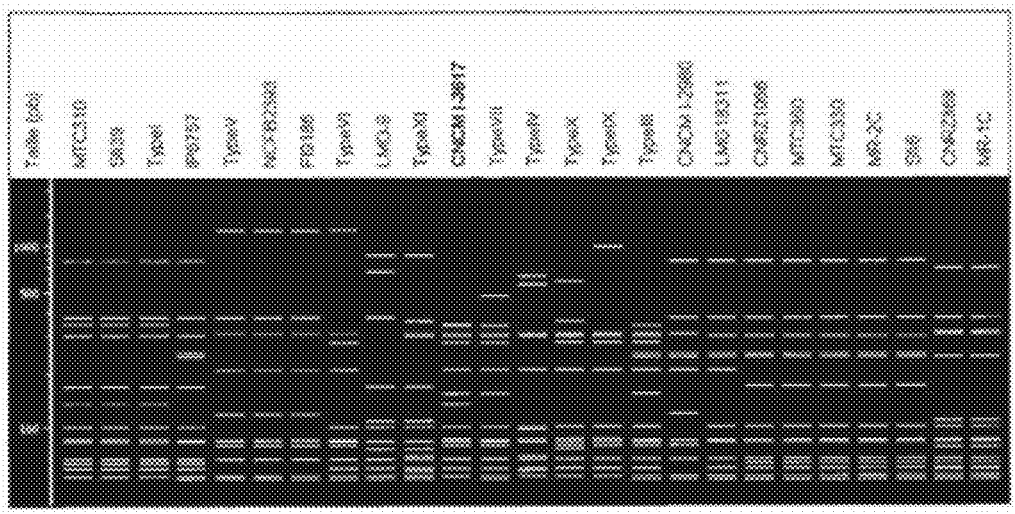

FIG. 3: In silico determination of the profiles obtained according to the epsAD method of the various strains of *S. thermophilic* the sequence of the eps locus of which is described in the literature. The images of the restriction profiles were generated using the NEBcutter tool with the following parameters: Gel Type=2% agarose; Marker=100 bp DNA Ladder; DNA Type=Unmethylated; L=102 mm. The GENBANK access numbers of these strains are: AF448502 (MTC310), AF373595 (Sfi39), AF410175 (Type I), AJ289861 (IP6757), AF454496 (Type V), YI7900 (NCFB 2393), AJ272341 (FI9186), AF454497 (Type VI), NZ_AAGS01000017 (LMD-9), AF454501 (Type XI), AF454498 (Type VII), AF454495 (Type IV), AF454500 (Type X), AF454499 (Type IX), AY057915 (Type III), CP000023 (LMG 18311), CF000024 (CNRZ 1066), AF434993 (MTC360), AF430847 (MTC330), AY061649 (MR-2C), U40830 (Sfib). Z98171 (CNRZ 368), AF448249 (MR-TC). The eps sequence of the strain CNCM I-2980 is, described in the Application WO2004/085607.

Figure 4:
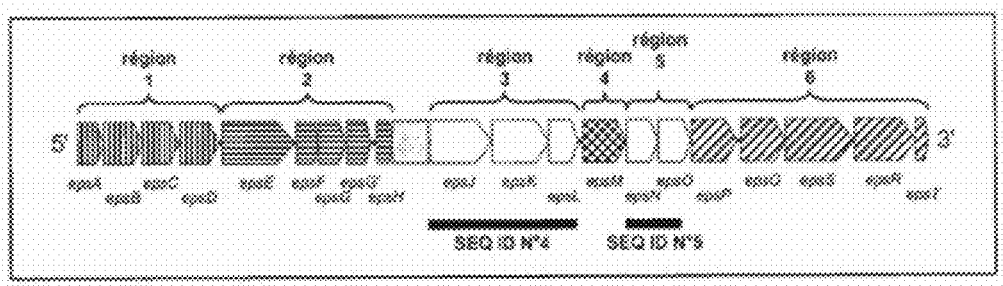

FIG. 4: Diagrammatic representation of the organization of the eps locus of the strain CNCM I-3617, corresponding to the sequence SEQ ID No3. The open reading frames (ORF) represented by vertical hatching (region 1) have significant similarities with the epsA-epsB-epsC-epsD genes situated at the start of the eps locus in the great majority of the strains of *S. thermophilus*. The ORFs represented by horizontal hatching (region 2) have significant similarities with the eps11E, eps11F, eps11G; and eps11H genes of the type XI strain. The ORFs represented by a chequered pattern (region 4) have significant similarities with the eps4F gene of the type IV strain. The grey rectangle between regions 2 and 3 represents a non-coding region having sequence homologies with a region of the eps locus of the type IV strain. The ORFs represented by diagonal hatching (region 6) have significant similarities with the epsP, epsQ, epsS, epsR and epsT genes of the CNRZ368 strain. The unshaded ORFs (regions 3 and 5) have no significant similarities with the eps genes described for other *S. thermophilus*. The two black bands at the bottom of the figure represent the position of the sequences SEQ ID No4 and SEQ ID No5.

EXAMPLES

Biological Material

Table 1 and Table 3 show some of the strains used for the study. Some of these strains are obtained from the Danisco collection of strains and phages (DGCC: Danisco Global Culture Collection). The preparation of cultures of these strains was carried out according to the standard methods of microbiology.

(for a journal article, see Broadbent et al., 2003). Flanked by the deoD (coding for a purine-nucleoside phosphorylase) and pgm (coding for a phospho-glucomutase) genes, all the clusters of eps genes in *S. thermophilus* are composed of a conserved proximal region (from the epsA gene to the epsD gene) and of a highly variable distal region. In spite of a conserved organization of the epsA-B-C-D genes, a significant sequence polymorphism exists in this region. The polymorphism of this region has been used to develop a tool for genetic typing of the strains of *S. thermophilus*: the epsAD method.

epsAD method: The tool developed is based on the specific amplification (PCR) of the epsA-B-C-D region followed by the analysis of its restriction polymorphism (RFLP). For this purpose primers have been determined which allow the PCR amplification of this region for the great majority of the strains of *S. thermophilus*. They have been determined by the alignment of the sequences of the epsAD region (cf. FIG. 2) and allow the amplification of a DNA fragment of approximately 2480 base pairs (bp). The genomic DNA of *S. thermophilus* is purified using the "DNeasy Tissue Kit" (Qiagen), then the epsAD region is amplified by PCR according to the following parameters:

Composition of the reaction mixture (50 µL): buffer for the DNA polymerase ×1, MgCl$_2$ 2 mM, dNTP 200 µM each, genomic DNA 100 to 500 ng, primer EPSA632 (5'-AAAT-gAATTCAgAgCAAgCACTTg-3' (SEQ ID No1)) 200 nM,

TABLE 1

Description of some of the strains used for the study

| Strain | Other name | Texturizing property[a] | Acidifying property[a] | Related strains[b] | Bibliographical references[c] |
|---|---|---|---|---|---|
| CNCM I-3617 | | Yes | Yes | Unknown | None |
| CNCM I-2980 | | Yes | Yes | DGCC2056 DGCC8013, DGCC8015 | WO2004/085607 |
| CNCM I-2423 | MTC310 | Yes | Yes | Sfi39, SY102 FI9186, Type I DGCC945 | Lemoine et al. (1997); Germond et al. (2001); Marshall et al. (2001) |
| CNCM I-2978 | MTC360 | Yes | No | Sfi6, CNCM I-733, CNCM I-734, CNCM I-735, IMDO1, 2, 3, NCFB859, EU21, MR-2C, DGCC7773 | Lemoine et al. (1997); Doco et al. (1990); Marshall et al. (2001); Stingele et al. (1996) |
| CNCM I-2423 | Type IV | Yes | No | Unknown | Rallu et al. (2002) |
| CNCM I-2429 | Type VII | Yes | No | Unknown | Rallu et al. (2002) |
| CNCM I-2979 | | Yes | No | CNRZ368 MR-1C | Bourgoin et al. (1999); Low et al. (1998) |
| DGCC7966 | | Yes | No | Unknown | None |
| DGCC7919 | | No | Yes | Unknown | None |
| DGCC7766 | | No | No | Unknown | None |

[a]on the basis of industrial use and the present study.
[b]on the basis of published sequence results of the eps locus and/or the structure of the polysaccharide and data internal to Danisco.
[c]on the strain studied and/or on related strains.

The Strain CNC 617 Belongs to a Novel Genetic Cluster

The recent determination of the complete sequence of the chromosome of two strains of *S. thermophilus* CNRZ1066 and LMG18311 shows a high level of conservation of the genetic content and the organization of the genes in this species) Bolotin et al., 2004). One of the rare regions exhibiting major genetic differences between these two strains corresponds to the eps locus which codes for the genes involved in the biosynthesis of exopolysaccharides. Moreover, a great diversity has already been described at the level of this genetic locus (cf. FIG. 1) since several eps sequences had been determined for various strains of *S. thermophilus* primer EPSD1064 (5'-gTCATgTCAACTTTATTAAggACg-3' (SEQ ID No2)) 200 nM, DNA polymerase 1.25 units, H$_2$O qsf 50 µL.

Amplification Parameters:
predenaturation at 94° C. for 1 min
35 cycles alternating denaturation at 94° C. for 30 s, hybridization at 56° C. for 30 s, elongation at 72° C. for 3 min
post-elongation at 72° C. for 6 min.

After amplification, the PCR product is checked by electrophoresis on 1.5% agarose gel. The size of the amplified product is approximately 2480 bp.

The sequence of the PCR fragment is determined (according to a method derived from Sanger et al., 1977) with CEQ8000 equipment (Beckman). The sequence is processed by the NEBcutter tool by selecting the restriction enzymes Mn/I, FokI and HindIII in order to establish its restriction profile in silico, and in particular in order to define the size of the restriction fragments.

For the strains of S. thermophilus the sequence of the eps locus of which is partially or completely available in the public databases (GENBANK for example), the in silico analysis of the theoretical restriction products of the PCR fragment of approximately 2480 bp with the restriction enzymes Mn/I, FokI and HindIII produces the restriction profiles shown in FIG. 3. These restriction profiles were established in silico on the basis of the sizes of the restriction fragments provided by the NEBcutter tool (cf. Table 2).

The restriction fragments are then analyzed by electrophoresis. Electrophoresis on agarose gel can be used. However, in order to remedy the low resolution power of this type of electrophoresis (precision +/−10%) and the difficulty of visualizing fragments smaller than 100 bp, methods with a higher resolution (+/−0.1 to 1%) such as micro-fluidic electrophoresis (Agilent) or capillary electrophoresis may be preferred.

These methods (in silico analysis of the restriction profile or electrophoresis analysis of the restriction fragments) were applied to several hundreds of strains from the Danisco collection of S. thermophilus strains and the reference strains described in the literature.

The strains which have the same restriction profile have been grouped together genetic clusters (or genetic groups) denoted CL-1 to CL-12. Comparison of the restriction pro-

TABLE 2

Size of the DNA fragments determined by in silico digestion of the epsAD fragment by the restriction enzymes MnlI, FokI and HindIII, for the strains of S. thermophilus the sequence of the epsA-B-C-D genes of which is available.

| Strain of S. thermophilus | GENBANK access number of the eps locus, or other reference | Size of the MnlI, FokI and HindIII digestion fragments of the epsAD region (size in base pairs determined by NEBcutter |
|---|---|---|
| MTC310 | AF448502 | 778; 371; 344; 299; 175; 142; 100; 79; 75; 42; 35; 23; 9 |
| Sfi39 | AF373595 | 778; 371; 344; 299; 175; 142; 100; 79; 75; 42; 35; 23; 9 |
| Type I | AF410175 | 778; 371; 344; 299; 175; 142; 100; 79; 75; 42; 35; 23; 9 |
| IP6757 | AJ289861 | 778; 371; 299; 247; 239; 175; 100; 76; 75; 42; 35; 23; 9; 3 |
| Type V | AF454496 | 1264; 374; 305; 210; 123; 76; 66; 42; 9; 3 |
| NCFB2393 | Y17900 | 1264; 374; 305; 210; 123; 76; 66; 42; 9; 3 |
| FI9186 | AJ272341 | 1264; 374; 305; 210; 123; 76; 66; 42; 9; 3 |
| Type VI | AF454497 | 1286; 305; 277; 210; 100; 76; 75; 66; 42; 23; 9; 3 |
| LMD-9 | NZ_AAGS01000017 | 848; 655; 371; 175; 111; 100; 75; 60; 42; 23; 9; 3 |
| Type XI | AF454501 | 851; 356; 305; 299; 175; 111; 100; 75; 60; 46; 42; 23; 20; 9; 3 |
| CNCM I-3617 | SEQ ID N°3 | 344; 341; 305; 299; 277; 210; 160; 142; 100; 79; 75; 66; 42; 23; 9 |
| Type VII | AF454498 | 486; 341; 305; 299; 277; 210; 160; 100; 76; 75; 66; 42; 23; 9; 3 |
| Type IV | AF454495 | 618; 551; 305; 299; 210; 100; 95; 79; 75; 46; 42; 23; 20; 9 |
| Type X | AF454500 | 571; 356; 305; 299; 277; 210; 100; 79; 75; 66; 60; 42; 23; 9 |
| Type IX | AF454499 | 987; 305; 299; 277; 210; 100; 79; 75; 66; 42; 23; 9 |
| Type III | AY057915 | 341; 305; 299; 277; 247; 239; 210; 160; 100; 76; 75; 66; 42; 23; 9; 3 |
| CNCM I-2980 | WO2004/085607 | 778; 374; 305; 247; 239; 210; 123; 76; 66; 42; 9; 3 |
| LMG18311 | CP000023 | 778; 371; 299; 247; 239; 210; 100; 76; 75; 42; 23; 9; 3 |
| CNRZ1066 | CP000024 | 778; 371; 299; 247; 239; 175; 100; 76; 75; 42; 35; 23; 9; 3 |
| MTC360 | AF434993 | 778; 371; 299; 247; 239; 175; 100; 76; 75; 42; 35; 23; 9; 3 |
| MTC330 | AF430847 | 778; 371; 299; 247; 239; 175; 100; 76; 75; 42; 35; 23; 9; 3 |
| MR-2C | AY061649 | 778; 371; 299; 247; 239; 175; 100; 76; 75; 42; 35; 23; 9; 3 |
| Sfi6 | U40830 | 778; 371; 299; 247; 239; 175; 100; 76; 75; 42; 35; 23; 9; 3 |
| CNRZ368 | Z98171 | 691; 371; 312; 305; 239; 112; 100; 76; 75; 63; 42; 35; 23; 22; 9; 3 |
| MR-1C | AF448249 | 691; 371; 312; 305; 239; 112; 100; 76; 75; 63; 42; 35; 23; 22; 9; 3 |

Alternatively, the PCR product can be digested by the restriction enzymes Mn/I, FokI and HindIII under the following conditions: PCR product 15 to 30 μL, buffer 2 (New England Biolabs)×1, bovine serum albumin (New England Biolabs)×1, enzyme Mn/I (New England Biolabs) 1 unit, enzyme FokI (New England Biolabs) 1 unit, enzyme HindIII (New England Biolabs) 1 unit, H$_2$O qsf 50 μL. Incubation at 37° C. for 1 hour.

files was carried out by means of Bionumerics software version 3.5. Table 3 summarizes some of the results obtained.

TABLEAU 3

Summary of the results of genotyping and lysotyping

| Strain | Genotype | Lysotype | Owner | Texturizing |
|---|---|---|---|---|
| CNCM I-3617 | CL-1 | Resistant | Danisco | YES |
| CNCM I-2423 | CL-2 | LT-2 | Danisco | YES |
| CNCM I-2426 | | | Danisco | YES |
| CNCM I-2424 | | | Danisco | YES |
| Sfi39 | | | Private collection | YES |
| DGCC945 | | | Danisco | YES |
| CNCM I-2432 | CL-3 | LT-4 | Danisco | YES |
| CNCM I-2978 | CL-4 | | Danisco | YES |
| DGCC7773 | | | Danisco | YES |
| CNRZ1066 | | | Public collection | YES |
| DGCC7785 | | | Danisco | YES |
| DGCC7788 | | | Danisco | YES |
| DGCC7966 | | | Danisco | YES |
| DGCC47 | | | Danisco | YES |
| CNCM I-2980 | CL-5 | LT-5 | Danisco | YES |
| DGCC2056 | | | Danisco | YES |
| DGCC8013 | | | Danisco | YES |
| DGCC8015 | | | Danisco | YES |
| DGCC7790 | CL-6 | LT-6 | Danisco | YES |
| DGCC7813 | | | Danisco | YES |
| CNCM I-2979 | | | Danisco | YES |
| CNRZ368 | | | Public collection | YES |
| MR-1C | | | University | YES |
| CNCM I-2429 | CL-7 | LT-7 | Danisco | YES |
| ATCC BAA-491 | CL-8 | LT-8 | Public collection | NO |
| DGCC7689 | | | Danisco | NO |
| DGCC1086 | | | Danisco | NO |
| SMQ-301 | CL-9 | | University | NO |
| DGCC7853 | | | Danisco | NO |
| DGCC7919 | CL-10 | LT-10 | Danisco | NO |
| DGCC7766 | CL-11 | LT-11 | Danisco | NO |
| DGCC7809 | CL-12 | LT-12 | Danisco | NO |

Method for determining the sensitivity of a strain to a bacteriophage: The sensitivity of a strain to a bacteriophage is established by the lysis plaque method. 100 µl of a culture of the strain to be tested and 100 µl of an appropriate dilution of a serum containing the bacteriophage to be studied are used in order to seed 5 ml of an agar medium under suffusion (0.6% agar weight/volume) M17+glucose supplemented at 10 mM with CaCl$_2$. The mixture is poured onto the surface of a solidified attar medium (1.5% agar weight/volume) M17+ glucose supplemented at 10 mM with CaCl$_2$. After incubation overnight at 42° C., the strain's sensitivity to the bacteriophage is evaluated by the presence of lysis plaques. The absence of lysis plaque signifies this strain's resistance to the bacteriophages tested. The spectrum of a strain's sensitivity to the bacteriophages, also called lysotype, is constituted by all of the sensitivities and resistances to the bacteriophages studied. A reference system with approximately sixty phages has been implemented in order to establish the lysotype of the strains of S. thermophilus in the Danisco collection. The strains which have the same lysotype have been grouped together in different groups denoted LT-n.

Some of the results are given in Table 3. It demonstrates in particular that the strains of the same genetic cluster virtually always have the same lysotype. The strain CNCM I-3617 belongs to a novel genetic group called CL-1 which has the very particular lysotype of being resistant to all the bacteriophages tested.

Sequence of the eps Locus

The genetic knowledge acquired with regard to S. thermophilus has shown that the eps locus is one of the major sites of heterogeneity between strains. This characteristic has already been exploited in part in order to develop the abovementioned genotyping method which uses the diversity in the epsA-B-C-D region which is the proximal region of the eps locus. An even greater diversity appears in the distal region of the eps locus (region encoding the glycosyl-transferases, see FIG. 1). This region gives the specificity of the exopolysaccharide and therefore induces at least in part the specificity of the strain's thickening power. This is therefore a region of the chromosome particularly indicated for unambiguously describing the strain CNCM I-3617 and the strains which are related to it. The nucleotide sequence of the eps locus of the strain CNCM I-3617 (starting from the epsA gene was obtained from a synthetic DNA fragment. This fragment was synthesized by PCR on a purified genomic DNA matrix of the strain CNCM I-3617 using two specific primers of conserved genes (deoD encoding a purine-nucleotide phosphorylase, and orf14.9 of unknown function) generally framing the eps locus in the S. thermophilus described in the literature. The sequence of 16037 bp originating from the strain CNCM I-3617 corresponds to the SEQ ID No3.

The sequences SEQ ID No4 and SEQ ID No5 (cf. FIG. 4) correspond respectively to the positions 6592 to 9391 and 10331 to 11373 of SEQ ID No3.

Genetic Organization of the eps Locus

FIG. 4 shows diagrammatically the genetic structure of the eps locus of the strain CNCM I-3617 established by analysis of its nucleotide sequence. The part upstream of the epsA open reading frame (ORF), the sequence of the start of the epsA ORF, and the part downstream of the epsT ORF are not known. Analysis of the sequence identifies 20 ORFs which are all oriented in the same direction. Due to their similarity of sequence with other known genes, and/or by the presence of specific protein units within products deduced from these ORFs, it is possible to attribute a putative function to them.

The structural analysis of the eps locus of the strain CNCM I-3617 shows that it possesses an overall organization similar to that of the eps loci already known (cf. FIG. 1).

The results of sequence comparison between the potential proteins deduced from the ORFs of the eps locus of CNCM I-3617 and those available in the public of databases (GENBANK) are summarized in Table 4. The eps locus of the strain CNCM I-3617 codes for proteins potentially involved in the synthesis of polysaccharide such as for example glycosyl-transferases.

On the basis of these data, 6 regions can be distinguished (region 1 to region 6, from the 5' end to the 3' end of the eps locus; see FIG. 4):

Region 1: this region is formed from 4 ORFs (epsA, epsB, epsC, epsD) for which the deduced proteins exhibit very great similarities (between 95.7 and 99.6%) with the proteins deduced from ORFs situated in the eps locus of strains of S. thermophilus.

Region 2: this region is formed from 5 ORFs (epsE, epsF, epsG, epsG' and epsH) for which the deduced proteins exhibit very great similarities (between 96.6 and 99.3% proteins deduced from ORFs situated in the eps locus of the type XI strain (GENBANK access no. A17454501).

Region 3: this region is formed from 3 ORFS (epsJ, epsK and epsL) for which the deduced proteins exhibit sufficient similarities (less than 81%) with proteins described in the literature to assign a probable function to them. However these ORFs are clearly distinct from ORFs already described in the literature.

Region 4: this region is formed from one ORF (epsM) for which the deduced protein exhibits very great similarities (95.4%) with the protein deduced from the eps4F ORF situated in the eps locus of the type IV strain.

Region 5: this region is formed from 2 ORFs (epsN and epsO) for which the deduced proteins exhibit sufficient similarities (less than 91%) with proteins of lactobacillae described in the literature to assign a probable function to them. However these ORFs are clearly distinct from ORFs already described in the literature in *S. thermophilus*.

Region 6: this region is formed from 5 ORFs (epsP, epsO, epsS, epsR and epsT) for which the deduced proteins exhibit very great similarities (between 98.9 and 100%) with the proteins deduced from ORFs situated in the eps locus of the strain CNRZ368 (GENBANK access no. Z98171).

Overall, the distal part of the eps locus resembles a hybrid assembly of genes certain of which had never previously been described.

TOP®, Eurial Poitouraine). The sterility of the solution is obtained by pasteurization for 10 min at 90° C. (at the core). The fermentation support thus obtained is inoculated with the strain to be tested at a rate of $10^6$ cfu/ml, then incubated at 43° C. (in a water bath). The pH is continuously monitored using a CINAC apparatus (Ysebaert).

The acidifying properties of the strains of *S. thermophilus* can be described by the maximum rate of acidification, Vm (pH unit/min (pHu/min)), calculated by the maximum value of the first derivative of the pH curve as a function of time. Under these operating conditions, it is estimated that this variable is characteristic of the strain. Its value is constant whatever the physiological state of the micro-upon inoculation of the milk and the level of seeding. Two groups of strains are distinguished, the strains with so-called slow acidification, the Vm of which is greater than –0.0100 pHu/min, and

TABLE 4

Analysis of the ORFs of the eps locus of the strain CNCM I-3617. The position corresponds to the nucleotides at the start and end of the ORF in the sequence SEQ ID N°3. The probable function is that of the proteins deduced from the ORF sequence. The best similarity is the protein or the deduced protein (the GENBANK access number of the protein sequence is indicated in parentheses) having the greatest similarity with the protein deduced from the ORF. The score is the percentage similarity obtained for the best similarity using the "blastp" tool

| ORF | Position | Probable function | Best Similarity | Score |
|---|---|---|---|---|
| epsA | 1 to 491 | Transcriptional Regulator | Eps10A (AAN63761), *S. thermophilus* Type X | 99.4 |
| epsB | 492 to 1223 | Polymerization and/or export of polysaccharides | Eps5B (AAN63698), *S. thermophilus* Type V | 99.6 |
| epsC | 1232 to 1924 | Polymerization and/or export of polysaccharides | Eps1C (AAN63508), *S. thermophilus* Type I | 97.0 |
| epsD | 1934 to 2674 | Polymerization and/or export of polysaccharides | Eps5D (AAN63700), *S. thermophilus* Type V | 99.2 |
| epsE | 2731 to 4098 | Undecaprenyl-phosphate glycosyl-1-phosphate transferase | Eps11E (AAN63787), *S. thermophilus* Type XI | 98.9 |
| epsF | 4131 to 4574 | Rhamnosyltransferase | Eps11F (AAN63788), *S. thermophilus* Type XI | 99.3 |
| epsG | 4546 to 5073 | Epimerase | Eps11G (AAN63789), *S. thermophilus* Type XI | 96.6 |
| epsG' | 5089 to 5553 | Epimerase | Eps11G (AAN63789), *S. thermophilus* Type XI | 96.8 |
| epsH | 5644 to 5940 | UDP-glucose 6-dehydrogenase | Eps11H (AAN63790), *S. thermophilus* Type XI | 98.9 |
| epsJ | 6661 to 7812 | UDP-galactopyranose mutase | Glf (ZP_00045853), *Lactobacillus gasseri* ATCC 33323 | 81.1 |
| epsK | 7814 to 8896 | Glycosyltransferase | EpsF (AAG44710), *Lactobacillus delbrueckii* subsp. *bulgaricus* Lfi5 | 64.9 |
| epsL | 8896 to 9441 | Glycosyltransferase | CpsI (CAC81257), *S. thermophilus* FI9186 | 65.7 |
| epsM | 8896 to 9441 | Glycosyltransferase | Eps4F (AAN63682), *S. thermophilus* Type IV | 95.4 |
| epsN | 9540 to 10370 | dTDP-4-dehydrohamnose reductase | RfbD (YP_619620), *Lactobacillus delbrueckii* subsp. *bulgaricus* ATCC 11842 | 81.4 |
| epsO | 10955 to 11563 | dTDP-4-dehydrorhamnose 3,5-epimerase | RfbC (NP_964906), *Lactobacillus johnsonii* NCC 533 | 90.6 |
| epsP | 11580 to 12422 | Glycosyltransferase | EpsP (CAB52238), *S. thermophilus* CNRZ368 | 99.3 |
| epsQ | 12519 to 13358 | Glycosyltransferase | EpsQ (CAB52237), *S. thermophilus* CNRZ368 | 98.9 |
| epsS | 13355 to 14641 | unknown | EpsS (CAB52236), *S. thermophilus* CNRZ368 | 99.5 |
| epsR | 14648 to 15790 | Glycosyltransferase | EpsR (CAB52235), *S. thermophilus* CNRZ368 | 100 |
| epsT | 15790 to 16037 | unknown | EpsT (CAB52234), *S. thermophilus* CNRZ368 | 100 |

Acidifying Property

The fermentation support is obtained by supplementing 100 ml of semi-skimmed UHT milk (Le Petit Vendéen®) with 3% (weight/volume) of skimmed milk powder (SUP'R the strains with so-called rapid acidification the Vm of which is less than –0.0100 pHu/min. The strain CNCM I-3617 clearly belongs to the group of the so-called rapid acidification strains (Table 5). This property is very often linked to the presence in the genome of the strains of a gene encoding the wall protease PrtS which could be detected in the genome of CNCM I-3617.

TABLE 5

Maximum rate of acidification of different strains of *Streptococcus thermophilus* evaluated under the operating conditions described.

| Strain | Maximum rate (x–1.E5 upH/min) | | prtS gene |
|---|---|---|---|
| | Average | Standard deviation | |
| CNCM I-2429 | 66 | 24 | absent |
| DGCC7966 | 68 | 12 | absent |
| CNCM I-2432 | 80 | 13 | absent |
| DGCC7766 | 82 | 13 | absent |
| CNCM I-2978 | 88 | 12 | absent |
| DGCC7773 | 92 | 17 | absent |
| CNCM I-2979 | 102 | 33 | absent |
| CNCM I-2423 | 129 | 24 | present |
| CNCM I-3617 | 144 | 7 | present |
| CNCM I-2980 | 167 | 27 | present |
| DGCC7919 | 190 | 22 | present |

Texturizing Property

The fermentation support obtained by supplementing 100 ml of semi-skimmed UHT milk (Le Petit Vendéen®) with 3% (weight/volume) of skimmed milk powder (SUP'R TOP®, Eurial Poitouraine). The sterility of the solution is obtained by pasteurization for 10 min at 90° C. (at the core). The fermentation support thus obtained is inoculated with the strain to be tested at a rate of $10^6$ cfu/ml, then incubated at 43° C. (in a water bath) until a pH of 4.6 is obtained. The pH is continuously monitored using a CINAC apparatus (Ysebaert). The fermented milks thus obtained are placed in a ventilated oven at 6° C., until they are analyzed. Two types of rheological measurements are carried out: viscosity and flow. The viscosity measurements are carried out at a temperature of 2° C. on fermented milks after storage for 1, 7, 14 and 28 days at 6° C. The equipment used is a RVF-type Brookfield® viscosimeter (Brookfield Engineering Laboratories, Inc.) mounted on a Helipath stand Brookfield Engineering Laboratories, Inc.). The viscosimeter is equipped with a type C needle and the oscillation speed applied to the needle is 10 rpm. The flow measurements are carried out at a temperature of 8° C. on previously-stirred fermented milks, after storage for 14 days at 6° C. The equipment used is an AR1000-N rheometer (TA Instrument) equipped with co-axial cylinders (Radius 1=15 mm, Radius 2=13.83 mm, Height=32 mm, Air gap=2 mm). For the ascending segment, the stress applied in a continuous sweep varies from 0 to 60 Pa for a duration of 1 min according to a linear mode. For the descending segment, the stress applied in a continuous sweep varies from 60 to 0 Pa for a duration of 1 min according to a linear mode. The values taken into account are the thixotropic area and the yield point; the latter is calculated according to the Casson model.

The texturizing ability of a strain can be evaluated in a first phase by a viscosity measurement of the curd obtained under the operating conditions described above. The recognized non-texturizing strains provide viscosity values close to 30 Pa·s while the texturizing strains exceed 40 Pa·s. This texturizing ability can be more or less pronounced (Table 6). For example the strain CNCM I-2979 produces a curd the viscosity of which reaches 42 Pa·s, and the strain DGCC7966 makes it possible to obtain a clearly higher viscosity, of 70 Pa·s. The strain CNCM I-3611 provides curds the viscosity of which amounts to 54 Pa·s (Table 6). This value places this strain among the group of strains with a texturizing ability fully comparable to the industrial strains currently used to devise lactic ferments for the production of yoghurts and fermented milks.

TABLE 6

Viscosity of the fermented milks obtained with the different strains tested, after storage at 6° C. for 14 days.

| | Viscosity in Pa · s | |
|---|---|---|
| Strain | Average | Standard deviation |
| DGCC7966 | 70.0 | Nd |
| DGCC7773 | 55.0 | 3.3 |
| CNCM I-3617 | 54.0 | 2.5 |
| CNCM I-2980 | 53.0 | 2.9 |
| CNCM I-2429 | 51.0 | 3.1 |
| CNCM I-2978 | 49.6 | 4.2 |
| CNCM I-2432 | 43.0 | 4.0 |
| CNCM I-2979 | 42.2 | 3.0 |
| CNCM I-2423 | 42.0 | 4.6 |
| DGCC7919 | 28.0 | Nd |
| DGCC7766 | 30.0 | Nd |

Nd: not determined

The rheological analyses using the AR1000-N rheometer made it possible to measure two rheological descriptors relevant for qualifying fermented milks: the yield point of the product (Pa) and the thixotropic area (Pa/s). These measurements are reported in Table 7 for each of the strains. For the fermented milk with the strain CNCM I-3617, the average values are 11.25 Pa and 352 Pa/s respectively. These values are significantly different from those measured on curds obtained with strains deemed non-texturizing (DGCC7766 or DGCC7919).

TABLEAU 7

Values of yield point and thixotropic area, Casson model, measurements by the AR1000-N on fermented dairy products with different strains after storage for 14 days at 6° C.

| | Yield point (Pa) | | Thixotropic area (Pa/s) | |
|---|---|---|---|---|
| Strain | Average | Standard deviation | Average | Standard deviation |
| CNCM I-2980 | 5.89 | 0.9 | 488 | 107 |
| CNCM I-2423 | 8.86 | 0.9 | 1344 | 574 |
| CNCM I-2978 | 10.51 | 0.4 | 728 | 153 |
| CNCM I-3617 | 11.25 | 0.4 | 352 | 53 |
| CNCM I-2432 | 12.27 | 1.3 | 1245 | 181 |
| CNCM I-2429 | 13.32 | 1.2 | 1215 | 255 |
| CNCM I-2979 | 13.56 | Nd | 1786 | 250 |
| DGCC7773 | 14.00 | Nd | 60 | Nd |
| DGCC7966 | 15.00 | Nd | 43 | Nd |
| DGCC7919 | 15.91 | 0.2 | 33100 | 1415 |
| DGCC7766 | 17.01 | 0.1 | 17083 | 1520 |

Nd: not determined

CONCLUSION

The strain CNCM I-3617 has several characteristics of interest for the construction of ferments and in particular for ferments used during the production of yoghurts or fermented milks. It exhibits a rare combination of functional properties (acidifying and thickening strain) and its lysotype is distinct from that of the other strains used in a standard manner for these applications.

BIBLIOGRAPHICAL REFERENCES

Rolotin A, Quinquis B, Renault P, Sorokin A, Ehrlich S D, Kulakauskas S, Lapidus A, Goltsman E, Mazur M, Pusch G D, Fonstein M, Overbeek R, Kyprides N, Purnellc B, Prozzi D, Ngui K, Masuy D, Haney F, Burteau S. Boutry M. Delcour J, Goffeau A, Hols P (2004).
Complete sequence and comparative genome analysis of the dairy bacterium *Streptococcus thermophilus*.
*Nat Biotechnol.* 22(12), 1554-1558.
Bourgoin F, Pluvinet A, Gintz B, Decaris B, Guedon G (1999).
Are horizontal transfers involved in the evolution of the *Streptococcus thermophilus* exopolysaccharide synthesis loci?
*Gene.* 233(1-2) 151-161
Broadbent J R, McMahon D J, Welker D L, Oberg, C J, Moineau S (2003).
Biochemistry, genetics, and applications of exopolysaccharide production in *Streptococcus* thermophilus: a review.
*J Dairy Sci.* 86(2), 407-423.
Doco T, Wieruszeski J M, Fournet B, Carcano D, Ramos P, Loones A (1990).
Structure of an exocellular polysaccharide produced by *Streptococcus thermophilus,*
*Carbohydr Res.* 198(2), 313-321.
Germond J E, Delley M, D'Amico N, Vincent S J (2001).
Heterologous expression and characterization of the exopolysaccharide from *Streptococcus thermophilus* Sfi39.
*Eur Biochem.* 268(19), 5149-5156.
Lemoine J, Chirat F, Wieruszeski J M, Strecker G, Favre N, Neeser J R (1997).
Structural characterization of the exocellular polysaccharides produced by *Streptococcus thermophilus* SFi39 and SFi12.
*Appl Environ Microbial.* 63(9), 3512-3518.
Low D, Ahlgren J A, Horne D, McMahon D J, Oberg C J, Broadbent 998).
Role of *Streptococcus thermophilus* MR-1C capsular exopolysaccharide in cheese moisture retention.
*Appl Environ Microbial.* 64(6), 2147-2151.
Marshall V M, Laws A P, Gu Y, Levander F, Radstrom P, De Vuyst Degeest B, Vaningelgem F, Dunn H, Elvin M (2001).
Exopolysaccharide-producing strains of thermophilic lactic acid bacteria cluster into groups according to their EPS structure.
*Lett App Microbiol.* 32(6), 433-437.
Rallu F, Taillez P, Ehrlich D, Renault P (2002).
Common scheme of evolution between eps clusters of the food bacteria *Streptococcus thermophilus* and cps clusters of the pathogenic streptococci.
Proc. 6th Am. Soc. Microbiol. Conf. on Streptococcal Genetics, Asheville, N.C. Page 112.
Sanger F, Nicklen S, Coulson A R (1977).
DNA sequencing with chain-terminating inhibitors.
*Proc Natl Acad Sci USA.* 74(12), 5463-5467.
Stingele F, Neeser J R, Mollet B (1996).
Identification and characterization of the eps (Exopolysaccharide) gene cluster from *Streptococcus thermophilus* Sfi6.
*J Bacteriol.* 178(6), 1680-1690.
Tatusova T A, Madden T L (1999).
BLAST 2 Sequences, a new tool for comparing protein and nucleotide sequences.
*FEMS Microbiol Lett.* 174(2), 247-250.

---

The invention claimed is:

1. A isolated strain of *Streptococcus thermophilus*, wherein said strain has an epsAD fragment which, after digestion by the restriction enzymes Mn/I, FokI and HindIII, has a restriction profile characterized by DNA fragments of 344±2 bp, 341±2 bp, 305±2 bp, 299±2 bp, 277±2 bp, 210±2 bp, 160±2 bp, 142±2 bp, 100±2 bp, 79±2 bp, 75±2 bp, 66±2 bp, 42±2 bp, 23±2 bp and 9±2 bp.

2. A isolated strain according to claim 1 comprising a nucleotide sequence having the nucleotide sequence of SEQ ID No4.

3. A isolated strain according to claim 1 comprising a nucleotide sequence having the nucleotide sequence of SEQ ID No5.

4. A isolated strain of *Streptococcus thermophilus* wherein said strain is texturizing and wherein said strain has an epsAD fragment which, after digestion by the restriction enzymes Mn/I, FokI and HindIII, has a restriction profile characterized by DNA fragments of 344±2 bp, 341±2 bp, 305±2 bp, 299±2 bp, 277±2 bp, 210±2 bp, 160±2 bp, 142±2 bp, 100±2 bp, 79±2 bp, 75±2 bp, 66±2 bp, 42±2 bp, 23±2 bp and 9±2 bp.

5. A isolated strain of *Streptococcus thermophilus* wherein said strain acidifies rapidly and wherein said strain has an epsAD fragment which, after digestion by the restriction enzymes Mn/I, FokI and HindIII, has a restriction profile characterized by DNA fragments of 344±2 bp, 341±2 bp, 305±2 bp, 299±2 bp, 277±2 bp, 210±2 bp, 160±2 bp, 142±2 bp, 100±2 bp, 79±2 bp, 75±2 bp, 66±2 bp, 42±2 bp, 23±2 bp and 9±2 bp.

6. The isolated strain of *Streptococcus thermophiles* deposited on 14 Jun. 2006 at the Collection Nationale of Culture of Microorganisms under no. CNCM 1-3617.

7. A bacterial composition comprising at least one isolated strain according to claim 1.

8. A process for producing a food product, a food complement, a dietary supplement or a product with probiotic properties comprising the step of adding or mixing at least one strain according to claim 1 in the formulation of said food product, food complement, dietary supplement or product with probiotic properties.

9. A process according to claim 8 in which the food product, the food complement, the dietary supplement or the product with probiotic properties is a dairy product, a meat product, a cereal product, a drink, a foam or a powder.

10. A food product, food complement, dietary supplement or product with probiotic properties comprising at least one strain according to claim 1 or the bacterial composition according to claim 7.

11. A dairy product comprising at least the strain according to claim 1 or the bacterial composition according to claim 7.

12. A dairy product according to claim 11 wherein said dairy product is a fermented milk, a yogurt, a matured cream, a cheese, a fromage frais, a milk drink, a dairy product retentate, a processed cheese, a cream dessert, a cottage cheese or an infant milk.

13. A dairy product according to claim 11 comprising milk of animal and/or plant origin.

\* \* \* \* \*